(12) United States Patent
Branthover et al.

(10) Patent No.: US 9,943,304 B2
(45) Date of Patent: Apr. 17, 2018

(54) SUTURE ANCHOR MANAGEMENT

(71) Applicant: Wright Medical Technology, Inc., Memphis, TN (US)

(72) Inventors: Lewis Pearce Branthover, Memphis, TN (US); Gary W. Lowery, Eads, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 225 days.

(21) Appl. No.: 14/651,487

(22) PCT Filed: May 27, 2015

(86) PCT No.: PCT/US2015/032617
§ 371 (c)(1),
(2) Date: Jun. 11, 2015

(87) PCT Pub. No.: WO2016/190859
PCT Pub. Date: Dec. 1, 2016

(65) Prior Publication Data
US 2017/0135688 A1 May 18, 2017

(51) Int. Cl.
*A61B 17/04* (2006.01)
*A61B 17/00* (2006.01)

(52) U.S. Cl.
CPC ............ *A61B 17/0401* (2013.01); *A61B 2017/00004* (2013.01); *A61B 2017/00477* (2013.01); *A61B 2017/00876* (2013.01); *A61B 2017/0409* (2013.01); *A61B 2017/0414* (2013.01); *A61B 2017/0441* (2013.01)

(58) Field of Classification Search
CPC ........ A61B 17/0401; A61B 2017/0409; A61B 2017/044; A61B 2017/0445; A61B 2017/0496; A61B 2017/06057
See application file for complete search history.

(56) References Cited

U.S. PATENT DOCUMENTS

| 5,002,550 A | 3/1991 | Li |
| 5,224,946 A | 7/1993 | Hayhurst et al. |

(Continued)

FOREIGN PATENT DOCUMENTS

| EP | 0835640 A1 | 4/1998 |
| EP | 2796097 A2 | 10/2014 |

(Continued)

OTHER PUBLICATIONS

International Search Report and Written Opinion issued for corresponding International application No. PCT/US2015/032617, dated Feb. 25, 2016, 15 pages.

(Continued)

*Primary Examiner* — Ashley Fishback
(74) *Attorney, Agent, or Firm* — Duane Morris LLP

(57) ABSTRACT

A suture management device comprises a handle defining at least a first door cavity, a shaft extending distally from the handle, and a suture anchor coupled to a distal end of the shaft. The suture anchor is configured to couple one or more sutures to a bone. A first releasable door is sized and configured to fit within the first door cavity. The first releasable door is releasably coupled to the handle. The first releasable door defining a suture channel extending longitudinally about the circumference of the releasable door. The suture channel is configured to receive the one or more sutures therein.

15 Claims, 30 Drawing Sheets

(56) References Cited

U.S. PATENT DOCUMENTS

| | | |
|---|---|---|
| 5,690,676 A | 11/1997 | Dipoto et al. |
| 5,948,000 A | 9/1999 | Larsen et al. |
| 6,951,565 B2 | 10/2005 | Keane et al. |
| 7,645,293 B2 | 1/2010 | Martinek et al. |
| 8,834,495 B2 | 9/2014 | White et al. |
| 2003/0204193 A1 | 10/2003 | Gabriel et al. |
| 2005/0240199 A1 | 10/2005 | Martinek et al. |
| 2007/0150003 A1 | 6/2007 | Dreyfuss et al. |
| 2008/0033460 A1 | 2/2008 | Ziniti et al. |
| 2008/0119874 A1 | 5/2008 | Merves |
| 2010/0069923 A1 | 3/2010 | Nguyen et al. |
| 2010/0305576 A1 | 12/2010 | Ferguson et al. |
| 2012/0041484 A1 | 2/2012 | Briganti et al. |
| 2012/0071719 A1 | 3/2012 | Shanley et al. |
| 2014/0277125 A1 | 9/2014 | Spivey et al. |
| 2014/0364862 A1 | 12/2014 | Bennett et al. |

FOREIGN PATENT DOCUMENTS

| | | |
|---|---|---|
| JP | 2010-508119 A | 3/2010 |
| JP | 2012-502737 A | 2/2012 |
| WO | 2008/054814 A2 | 5/2008 |
| WO | 2010/033332 A1 | 3/2010 |
| WO | WO 2014/164605 A1 | 10/2014 |

OTHER PUBLICATIONS

International Search Report and Written Opinion issued for International application No. PCT/US2015/033177, dated Nov. 17, 2015, 15 pages.

Examination Report No. 1 dated Apr. 15, 2016, in connection with Australian patent application No. 2015203347, 5 pages.

Examination Report No. 1 dated Apr. 15, 2016, in connection with corresponding Australian patent application No. 2015203353, 6 pages.

International Search Report and Written Opinion issued in connection with International Application No. PCT/US2015/032971, dated Feb. 26, 2016, 17 pages.

Office Action issued in connection with Canadian patent application No. 2,895,812, dated Jul. 8, 2016, 7 pages.

Office Action issued in connection with Canadian patent application No. 2,895,713, dated Jul. 26, 2016, 9 pages.

Office Action issued in connection with Australian patent application No. 2015323847, dated Sep. 9, 2016, 7 pages.

Office Action issued for corresponding Canadian patent application No. 2,924,204, dated Mar. 21, 2017, 5 pages.

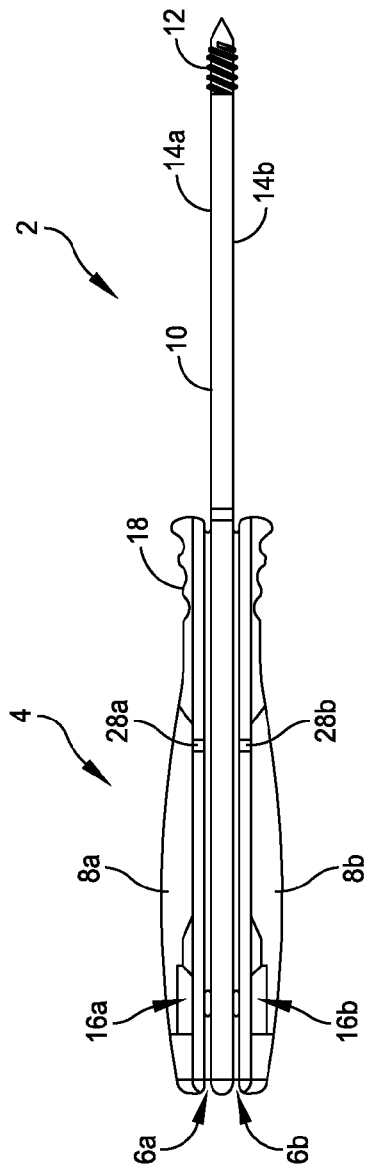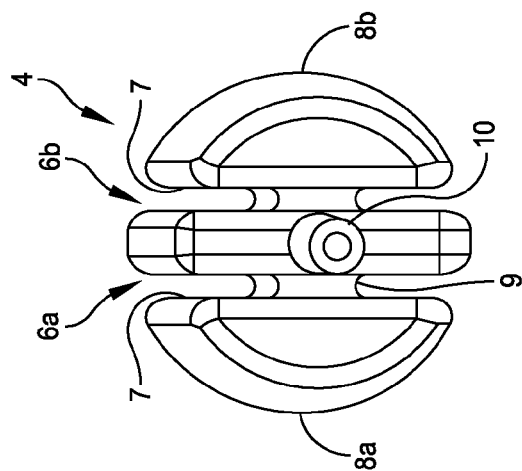

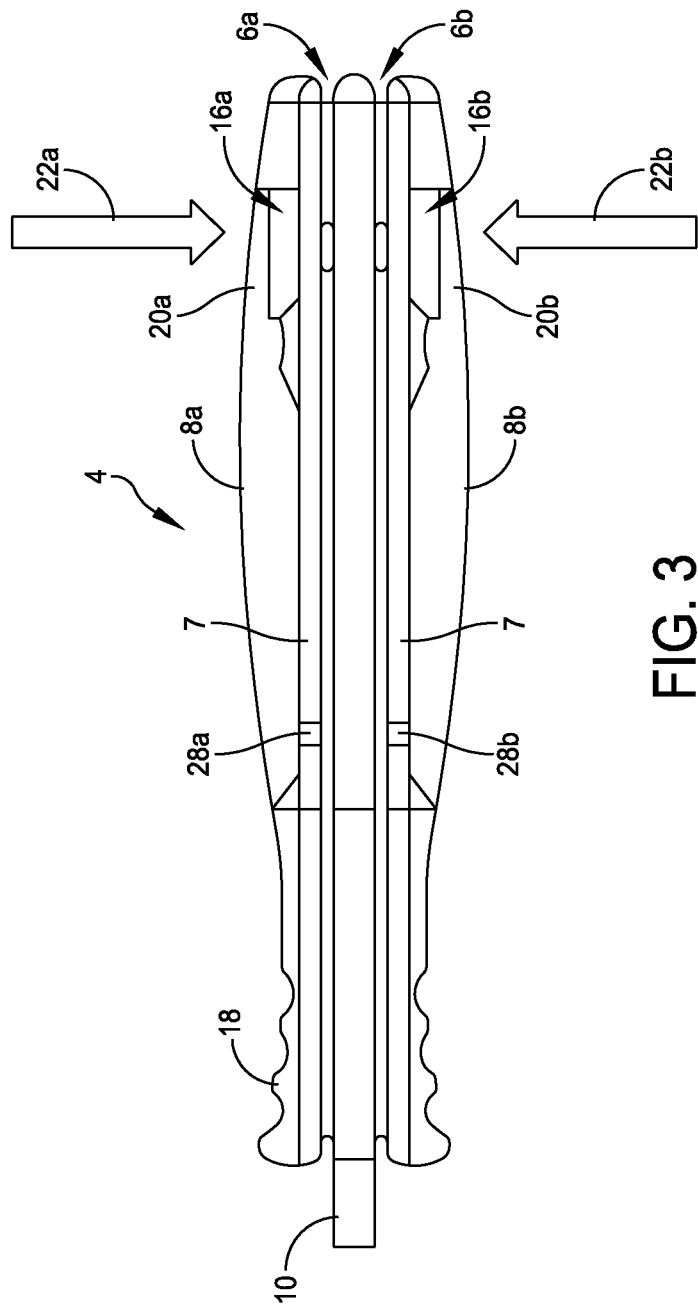

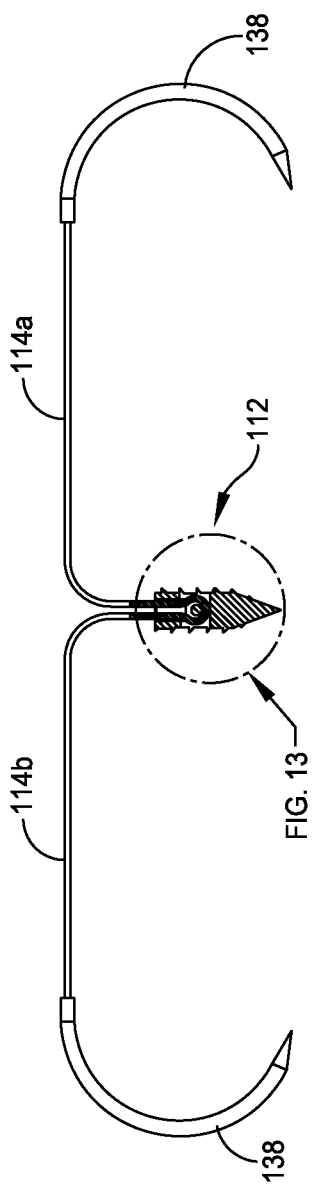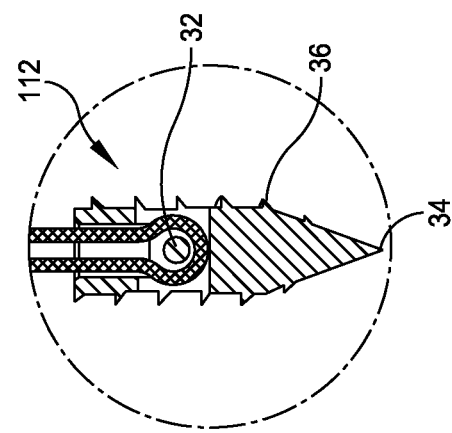
FIG. 14
FIG. 13

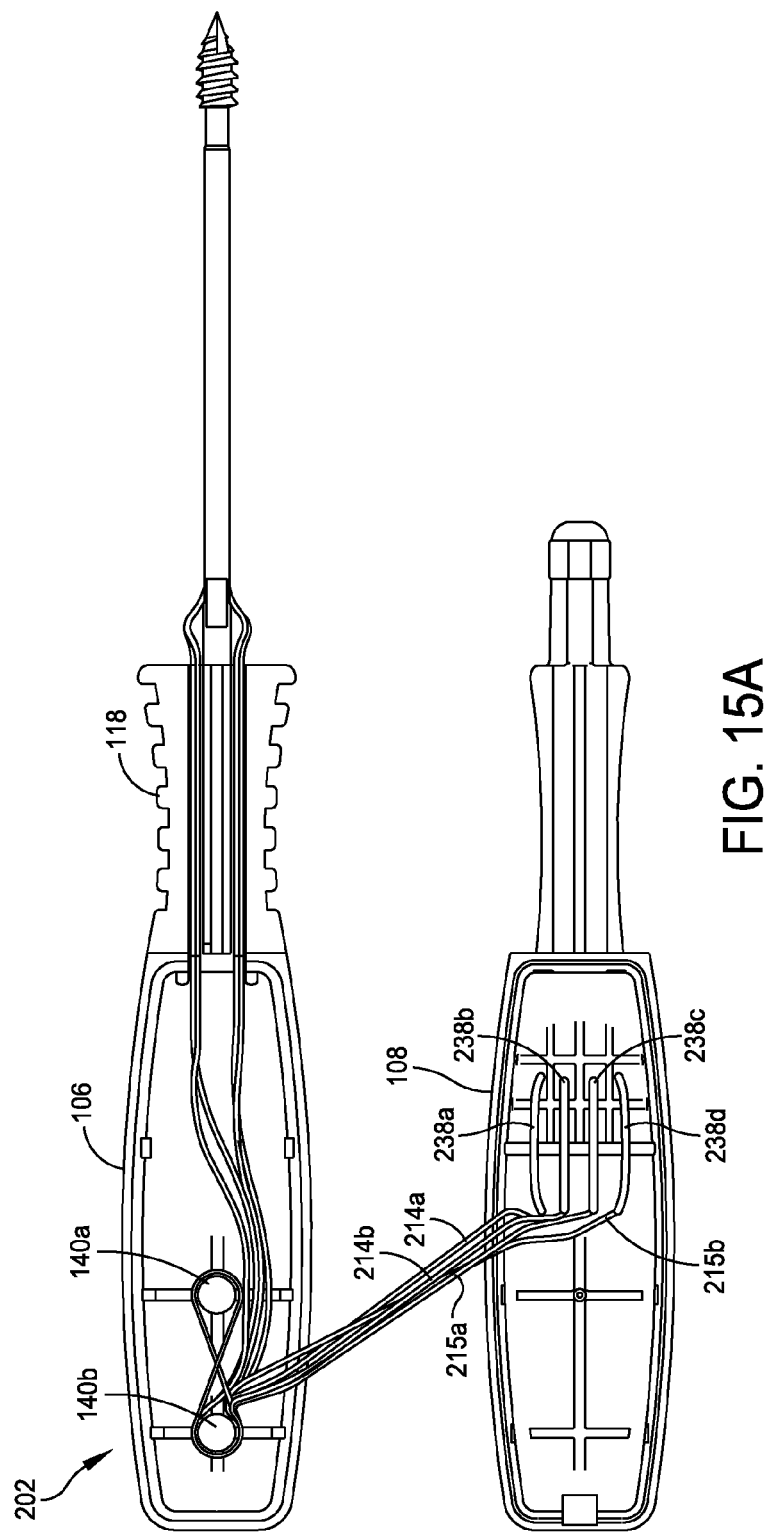
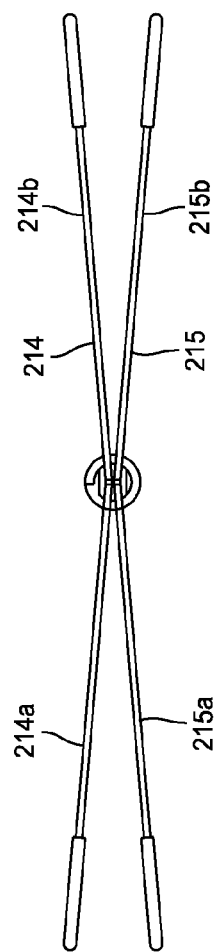
FIG. 15A
FIG. 16

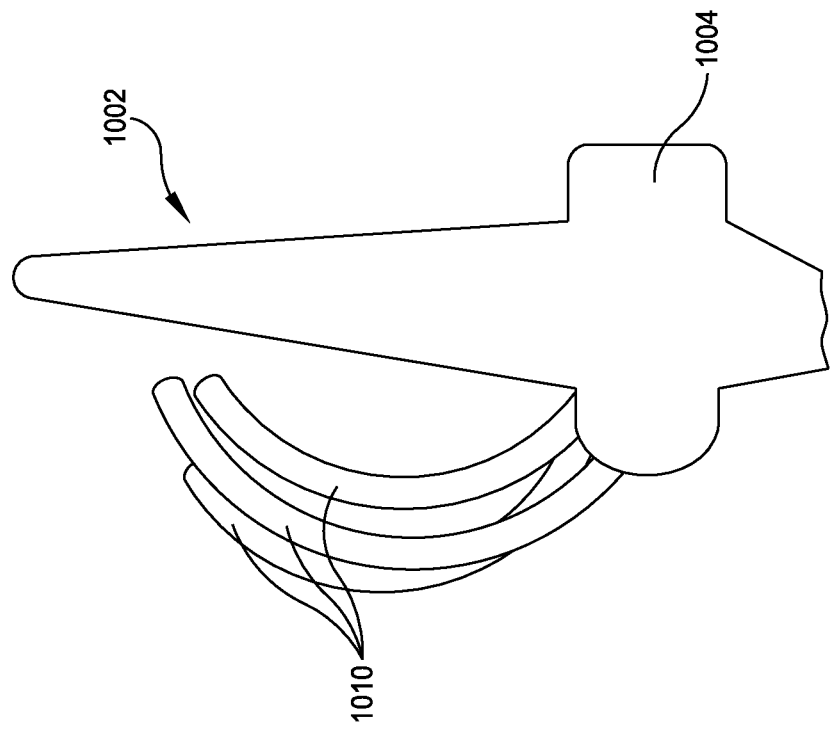
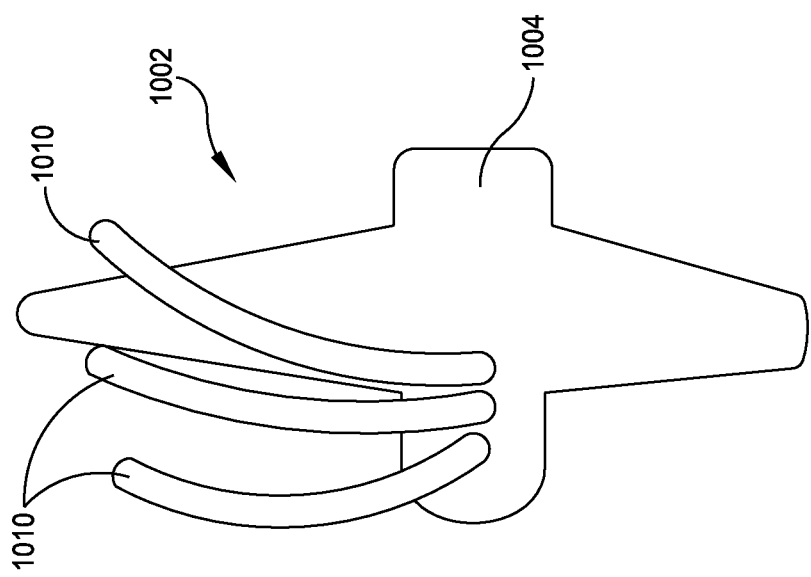
FIG. 28B
FIG. 28A

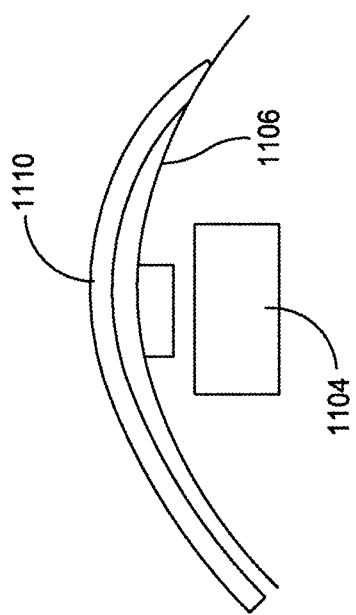

US 9,943,304 B2

SUTURE ANCHOR MANAGEMENT

CROSS-REFERENCE TO RELATED CASES

This application is a national phase entry under 35 U.S.C. § 371 of international patent application No. PCT/US15/32617, filed May 27, 2015, the entirety of which is herein incorporated by reference.

BACKGROUND

Detachment of tissue, such as ligaments, tendons, or other soft tissue from a bone can occur due to injury, surgery, bone deterioration, etc. The detached tissue must be reattached to the bone in order to allow the injury to properly heal. A suture and anchor system may be used to reattach the soft tissue to the bone. A suture anchor having one or more sutures attached thereto is driven into a bone. The sutures are then used to reattach the soft tissue to the bone. The sutures may include needles for passing the suture through the soft tissue.

During deployment and reattachment, management of the location and position of sutures is important. For example, multiple sutures may be attached to the suture anchor and may need to be maintained in a relative position during implantation of the suture anchor. Additionally, the sutures must be maintained in an easily accessible position while not interfering with a clinician's placement and deployment of a suture anchor.

SUMMARY

In various embodiments, a suture management device is disclosed. The suture management device comprises a handle defining at least a first door cavity, a shaft extending distally from the handle, and a suture anchor coupled to a distal end of the shaft. The suture anchor is configured to couple one or more sutures to a bone. A first releasable door is sized and configured to fit within the first door cavity. The first releasable door is releasably coupled to the handle. The first releasable door defining a suture channel extending longitudinally about the circumference of the releasable door. The suture channel is configured to receive the one or more sutures therein.

In various embodiments, a system is disclosed. The system comprises a suture management device. The suture management device includes a handle defining at least a first door cavity, a shaft extending distally from the handle, a suture anchor coupled to a distal end of the shaft, and a first releasable door sized and configured to fit within the first door cavity. The first releasable door is releasably coupled to the handle. The first releasable door defines a suture channel. The suture channel extends longitudinally about the circumference of the releasable door. One or more sutures coupled to the suture anchor. The one or more sutures extend proximally from the suture anchor. At least a first end of each of the one or more sutures is coupled to the suture channel. One or more needles coupled to a proximal end of the one or more sutures.

In various embodiments, a method is disclosed. The method comprises inserting a suture anchor into a bone using a suture management system. The suture management system comprises a handle having a shaft extending from a distal side of the handle. The suture anchor is releasably coupled to a distal end of the shaft. A first handle portion is released from a second handle portion. The first handle portion comprises a first post and a second post having a predetermined spacing. One or more sutures are unraveled from the first post and the second post. At least one suture extends proximally from the suture anchor along the shaft to the handle. The at least one suture is wrapped around the first and second posts to maintain the suture in a fixed position when the first body portion is coupled to the second body portion.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 1 illustrates one embodiment of a suture management device.

FIG. 2 illustrates a front view of the suture management device of FIG. 1.

FIG. 3 illustrates a top view of the suture management device of FIG. 1 having a first door and a second door in a closed position

FIG. 13 illustrates one embodiment of a suture anchor configured to couple to a distal end of a shaft of the suture management device of FIG. 10.

FIG. 14 illustrates one embodiment of the suture anchor of FIG. 13 having a suture including a first end and a second end coupled thereto.

FIG. 15A illustrates one embodiment of the suture management device of FIG. 10 having the first handle portion separated from the second handle portion to deploy a plurality of sutures.

FIG. 16 illustrates one embodiment of the suture anchor of FIG. 13 having a plurality of sutures coupled thereto.

FIG. 28A illustrates one embodiment of push-fit suture holder.

FIG. 28B illustrates a side view of the push-fit suture holder of FIG. 28A.

FIG. 29C illustrates a side view of the magnetic suture holder of FIG. 29B.

DETAILED DESCRIPTION

Figure 4:
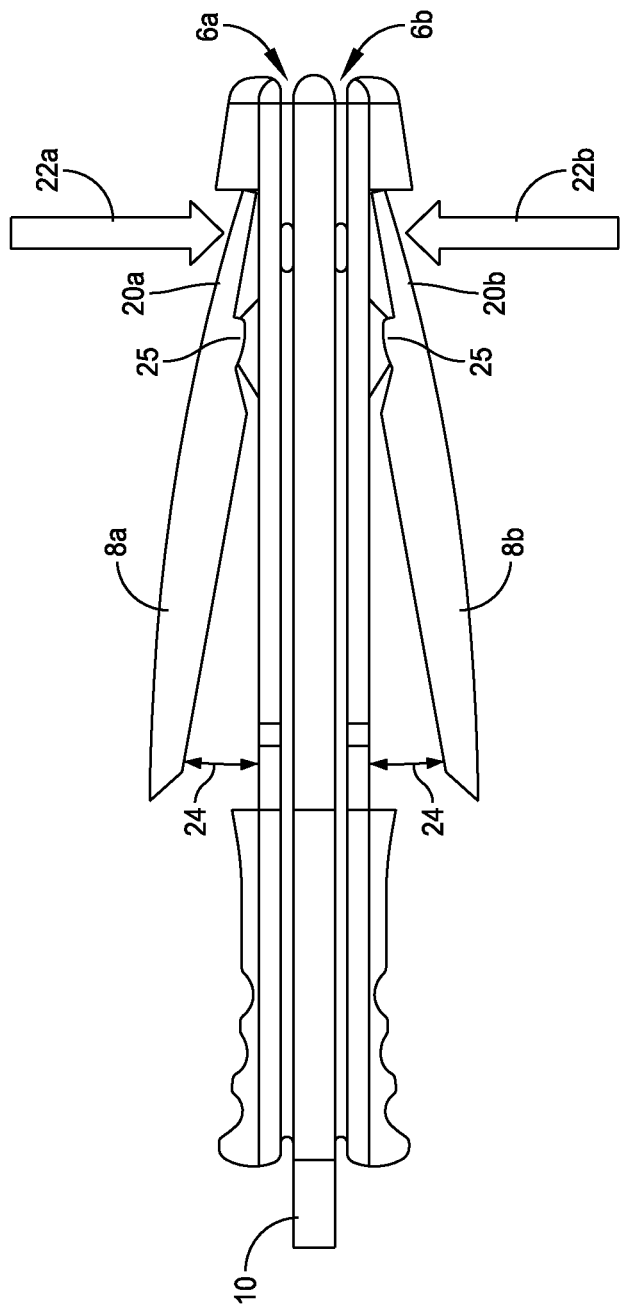
FIG. 4 illustrates a top view of the suture management device of FIG. 1 having a first door and a second door in an open position.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides suture delivery and management systems. The suture delivery and management systems generally comprise a device for delivering a suture anchor to a treatment site while maintaining one or more sutures in a predetermined arrangement. The suture delivery and management system prevents tangling of the sutures during implantation of the suture anchor and provides easily accessible storage for one or more sutures and/or needles coupled to one or more ends of the sutures.

FIG. 1 illustrates one embodiment of a suture management device 2. The suture management device 2 comprises a handle 4 having a proximal end and a distal end. A shaft 10 extends distally from the distal end of the handle 4. A suture anchor 12 is coupled to the distal end of the shaft 10. The handle 4 comprises a pair of elongate grooves 6a, 6b. In some embodiments, the elongate grooves 6a, 6b are circumferential slots that extend about the entire longitudinal circumference of the handle 4. The elongate grooves 6a, 6b are sized and configured to receive at least one suture end 14a, 14b therein. Each of the elongate grooves 6a, 6b comprises side-walls 7 and a central core 9 about which the suture ends 14a, 14b may be wrapped (see FIG. 2).

In some embodiments, a suture 14 having a first end 14a and a second end 14b extends from the suture anchor 12 along the outer surface of the shaft 10 to the handle 4. For example, in some embodiments, the suture 14 is coupled to a suture anchor 12 located at a distal end of the shaft 10. In some embodiments, the shaft 10 comprises one or more channels sized and configured to receive at least one suture therein, such that the ends 14a, 14b of the sutures 14 are flush with the outer surface of the shaft 10. The channels may extend partially or entirely along the length of the shaft 10. In some embodiments, the suture 14 may extend through a cannula defined by the shaft 10. In some embodiments, a suture 14 is coupled to the suture anchor 12 at a mid-point of the suture 14. A first end of the suture 14a and a second end of the suture 14b extend proximally from the suture anchor 12. Although the first end 14a and the second end 14b are illustrated as having equal lengths, it will be appreciated that the lengths of the first end 14a and the second end 14b may be different and/or variable.

In some embodiments, the suture ends extend proximally from the shaft 10 into the plurality of grooves 6a, 6b formed in the handle 4. For example, the first end 14a may extend into a first elongate groove 6a and the second end 14b may extend into a second elongate groove 6b. The first and second ends 14a, 14b are wrapped around the handle 4 within the elongate grooves 6a, 6b to secure the suture ends 14a, 14b to the handle 4. The suture ends 14a, 14b may be wrapped around the handle 4 within the elongate grooves 6a, 6b one or more times, for example, depending on the length of the suture. For example, in some embodiments, the suture 14 may have a predetermined length of about 24". Each of the suture ends 14a, 14b may comprise a length of about 12" and/or may comprise different lengths.

In some embodiments, each of the elongate grooves 6a, 6b comprises a suture slot 28a, 28b formed on a side-wall 7 of the elongate groove 6a, 6b. Each suture slot 28a, 28b is sized and configured to allow a suture ends 14a, 14b to exit the elongate groove 6a, 6b and extend into an area defined by a first door 8a or second door 8b formed on the handle 4. The doors 8a, 8b may comprise pivoting doors configured to sit flush with the handle 4 in a closed position and pivot to an open position when a force is applied. A portion of each suture end 14a, 14b extends into a cavity 26 defined between the doors 8a, 8b and the handle 4. The suture ends 14a, 14b may be coupled to needles (see FIG. 8) located within the cavities 26 defined by the first and second doors 8a, 8b and the handle 4. The needles and/or the doors 8a, 8b maintain tension on the sutures end 14a, 14b to maintain the suture ends 14a, 14b in the elongate grooves 6a, 6b. When the doors 8a, 8b are opened, tension on the suture ends 14a, 14b is released, causing the suture ends 14a, 14b and needles 38 coupled to the suture ends 14a, 14b to fall out of the cavity 26. The suture ends 14a, 14b may be unwrapped from elongate grooves 6a, 6b after being released from the cavity 26. After the suture 14 is removed, the handle 4 and the shaft 10 may be discarded.

In some embodiments, a suture anchor 12 is coupled to the distal end of the shaft 10. The suture anchor 12 is configured for implantation into a bone. The suture anchor 12 may comprise any suitable anchor, such as, for example, a bone screw, a pin, a bone tag, a staple, and/or any other suitable anchor. In operation, a clinician drives the suture anchor 12 into a bone using the handle 4 and the shaft 10. The suture anchor 12 may be driven into a bone that, for example, has had one or more ligaments, tendons, and/or other connective tissue disconnected therefrom, for example, due to an accident, surgery, and/or any other cause. After the suture anchor 12 is anchored to the bone, the suture 14 may be released from the suture management device 2 and used to reattach tissue to the bone.

FIG. 2 illustrates a front view of the suture management device 2 of FIG. 1. As shown in FIG. 2, the elongate grooves 6a, 6b extend about the longitudinal circumference of the handle 4 to define continuous grooves for receiving a suture therein. The suture ends 14a, 14b may be wrapped about the elongate grooves 6a, 6b any number of times depending on the length of the suture. In some embodiments, the depth of the elongate grooves 6a, 6b may comprise a predetermined depth sufficient to receive a plurality of sutures a predetermined number of times about the handle 4. In some embodiments, the shaft 10 extends through the handle 4.

FIG. 3 illustrates a top view of the suture management device 2 having the first door 8a and the second door 8b in a closed position. The suture ends 14a, 14b (see FIG. 1) extend from the shaft 10 into the elongate grooves 6a, 6b and wrap around the handle 4 a predetermined number of times. The suture ends 14a, 14b pass through the suture slots 28a, 28b and extend into an area between the doors 8a, 8b and the handle 4. The suture ends 14a, 14b may be coupled to needles 38 stored within the doors 8a, 8b. The doors 8a, 8b maintain tension on the suture 14 in a closed position. The doors 8a, 8b may be transitioned from a closed position to an open position (see FIG. 4) by applying a force 22 to proximal sections 20a, 20b of the doors 8a, 8b.

In some embodiments, each of the doors 8a, 8b are coupled to a pivot point 25a, 25b defined by the handle 4. A force 22 applied to the proximal sections 20a, 20b causes the doors 8a, 8b to pivot open about the pivot point 25. The proximal sections 20a, 20b pivot into cavities 16a, 16b formed in the handle 4. In some embodiments, a tensioning device 30a, 30b, such as, for example, a spring, may be located within each of the cavities 16a, 16b to bias the doors 8a, 8b to a closed position (see FIG. 6). The springs 30a, 30b may be selected such that a minimum force is required to pivot the doors 8a, 8b from the closed position to the open position. When the minimum force is applied, a distal section of the doors 8a, 8b pivots away from the handle 4. FIG. 4 illustrates the doors 8a, 8b in an open position. The doors 8a, 8b may be opened to a predetermined angle 24. In the illustrated embodiments, the first door 8a and the second door 8b open to the same predetermined angle 24, although in some embodiments the first door 8a and the second door 8b may open to different angles. When the doors 8a, 8b are in the open position, one or more needles 38 may be released from the doors 8a, 8b and the sutures 14a, 14b removed from the handle 4. The handle 4 and the shaft 10 may be discarded once the sutures are removed. Although the tensioning devices 30a, 30b are described herein as springs, it will be recognized that any suitable tensioning device may be used to apply a biasing force to the doors 8a, 8b. For example, in some embodiments, the tensioning devices 30a, 30b may comprise one or more springs, elastic materials (for example, silicone) that are compressed by opening the doors 8a, 8b, rubber band or other elastic coupler, torsion springs, and/or any other tensioning devices. In some embodiments, the first door 8a and the second door 8b may comprise a single piece having thin connecting section that maintains the first and second doors 8a, 8b in a first, closed position. The thin connecting section is flexible and a force applied the doors 8a, 8b causes the thin connecting section to flex, allowing the first and second doors 8a, 8b to transition to a second, open position.

Figure 5:
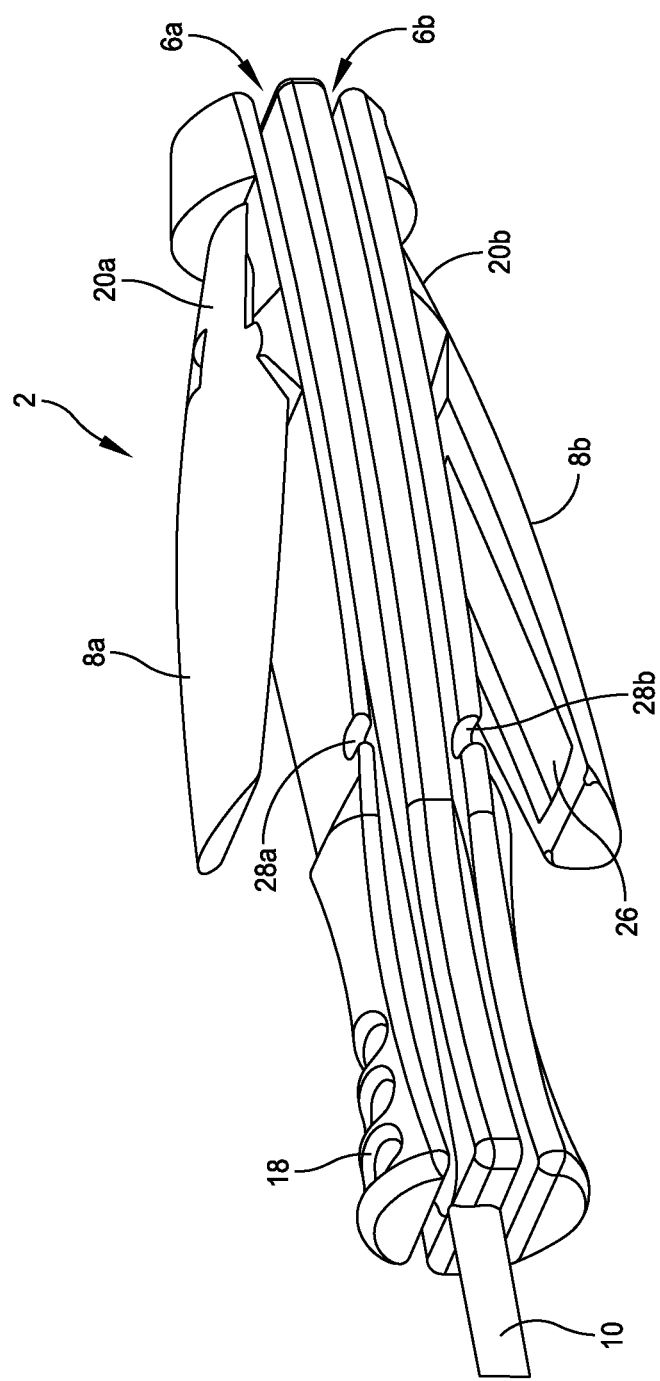
FIG. 5 illustrates a perspective view of the suture management device of FIG. 1 having the first door and the second door in an open position.

FIG. 5 illustrates a perspective view of the suture management device 2 having the doors 8a, 8b in an open position. The door 8a, 8b each define a cavity 26 sized and configured to receive one or more needles 38 and/or suture ends 14a, 14b therein. In some embodiments, a needle holder (not shown) is located within the cavity 26. The needle holder may comprise any suitable needle retention device. For example, the needle holder may comprise a force-fit suture holder (see FIGS. 27A-27B), a press-fit suture holder (see FIGS. 28A-28B), a magnetic suture holder (see FIGS. 29A-29B), and/or any other suitable needle storage system.

After the doors 8a, 8b are pivoted to an open position, the needles 38 may be removed from the cavity 26 and the suture ends 14a, 14b unwound from the handle 4. In some embodiments, the needles 38 and/or the suture ends 14a, 14b may be loosely stored within the cavity 26 and may fall out of the cavity 26 when the doors 8a, 8b are pivoted to an open position. The handle 4 may be discarded after the suture ends 14a, 14b are removed. The suture 14 is coupled to the anchor 12, which is anchored to the bone. The suture can be used to couple one or more tissue sections to the bone. For example, in some embodiments, the suture ends 14a, 14b may couple one or more ligaments, tendons, and/or other connective tissue to a bone. The suture 14 may comprise a degradable suture that dissolves over a predetermined time, such as, for example, a sufficient time for the tissue to naturally reattach to the bone.

Figure 6:
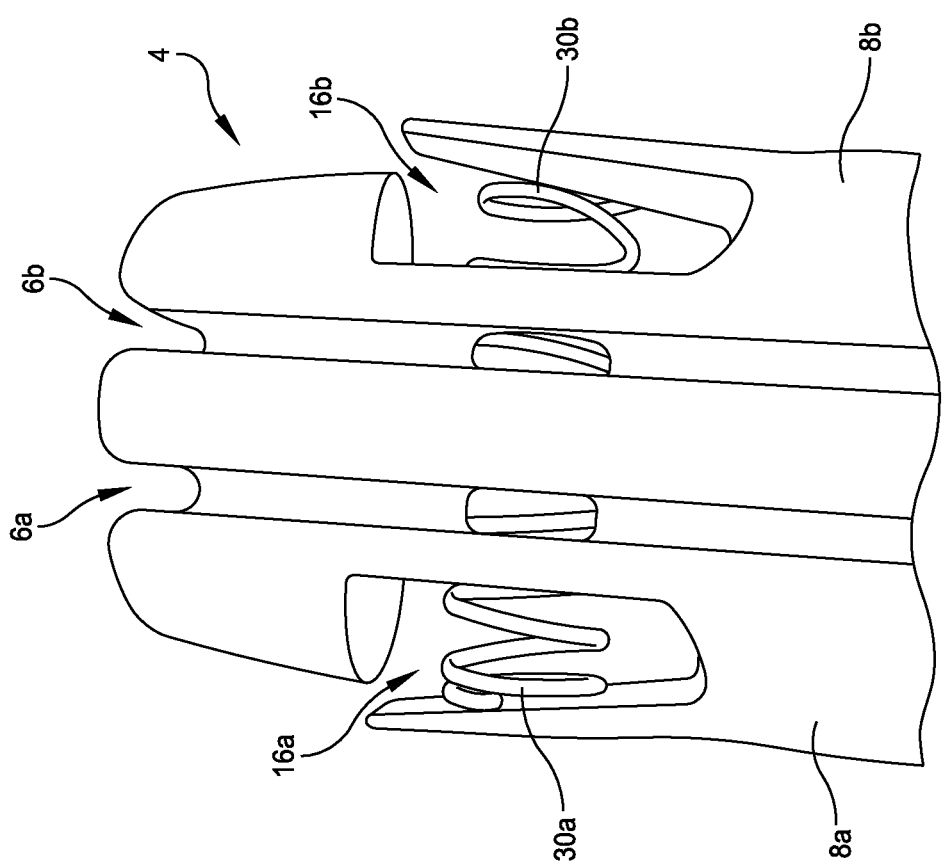
FIG. 6 illustrates a top-down view of a rear portion of the suture management device of FIG. 1.

FIG. 6 illustrates one embodiment of a proximal portion of the handle 4 of the suture management device 2. A first spring 30a and a second spring 30b are located within the pivot cavities 16a, 16b defined by the handle 4. The first and second springs 30a, 30b extend at least partially into and are anchored to the handle 4. In some embodiments, a single spring extends through an aperture in the handle 4 and into the cavities 16a, 16b. The springs 30a, 30b are configured to apply a biasing force to the doors 8a, 8b to maintain the doors 8a, 8b in a closed position. In order to pivot the doors 8a, 8b to an open position, a predetermined force must be applied to the handles 8a, 8b to overcome the biasing force applied by the springs 30a, 30b. In some embodiments, the handle 4 comprises a locking mechanism for locking the doors 8a, 8b into an open position after the biasing force is overcome. For example, in some embodiments, rivets (not shown) are coupled to the doors 8a, 8b and/or the handle 4 to lock the doors in an open position after the minimum force is applied.

Figure 7:
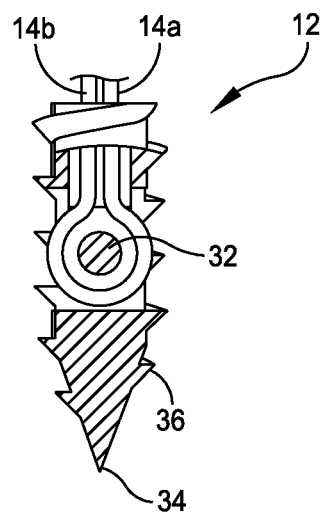
FIG. 7 illustrates one embodiment of a suture anchor configured to couple to a distal end of a shaft of the suture management device of FIG. 1.

FIG. 7 illustrates one embodiment of a suture anchor 12 configured to be releasably coupled to the shaft 10 of the suture management device 2. The suture anchor 12 is sized and configured to be driven into a bone. The suture anchor 12 comprises a suture fastener 32 configured to anchor one or more sutures 14 to the suture anchor 12. The suture fastener 32 may comprise, for example, an eyelet, a beam, and/or any other suitable fastener. In some embodiments, the suture 14 is coupled to the suture fastener 32 at a mid-point of the suture 14. The first end 14a and the second end 14b of the suture each extend proximally from the suture anchor 12 towards the handle 4. In some embodiments, the suture anchor 12 comprises a sharp distal end 34 and a thread 36. The sharp distal end 34 is configured to be driven into a bone, for example, by rotating the handle 4 and the shaft 10. The suture anchor 12 is driven to a predetermined depth sufficient to anchor the suture 14 to the bone. The suture anchor 12 is separable from the shaft 10 such that the suture anchor 12 may be retained in the bone when the suture management device 2 is removed from the treatment site. Although the suture anchor 12 is illustrated as a bone screw, it will be recognized that any suitable anchor may be used to couple the suture 14 to the bone. For example, in some embodiments, the suture anchor 12 can comprise a screw, a pin, a bone tag, a staple, and/or any other suitable anchor.

Figure 8:
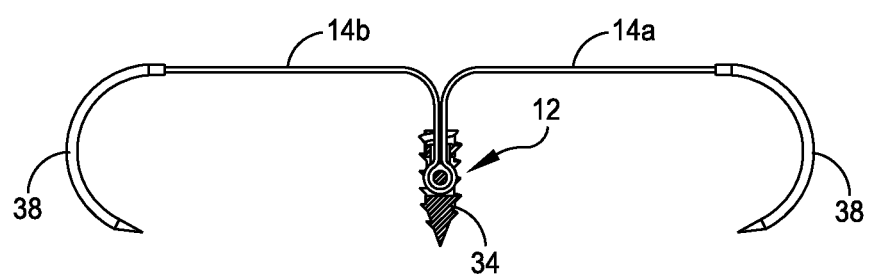
FIG. 8 illustrates the suture anchor of FIG. 7 having a plurality of sutures coupled thereto.

FIG. 8 illustrates one embodiment of the suture anchor 12 coupled to a suture 14. The suture 14 is coupled to the suture anchor 12 at a mid-point of the suture 14. A first end 14a and a second end 14b extend proximally from the suture anchor 12. Needles 38 are coupled to each of the ends 14a, 14b at a proximal end. When the suture anchor 12 is implanted into a bone, the suture ends 14a, 14b extend from the bone and may be used to attach one or more tissue sections to the bone. Although a single suture is illustrated, it will be appreciated by those skilled in the art that any number of sutures and needles may be coupled to the suture anchor 12. In some embodiments, the suture 14 is provided without needles 38 coupled thereto.

Figure 9:
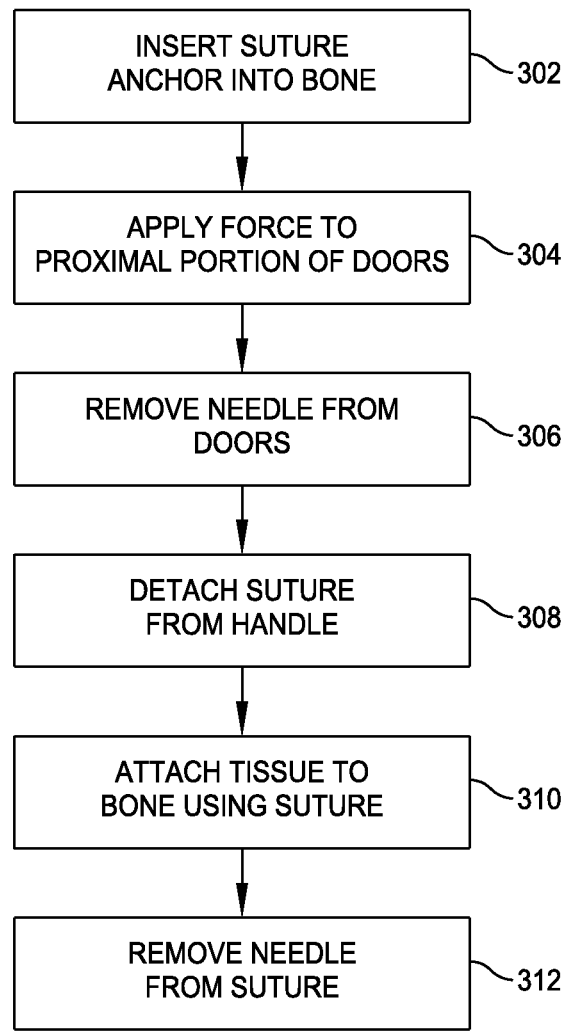
FIG. 9 is a flowchart illustrating one embodiment of a method for attaching tissue to a bone using the embodiments of a suture management system illustrated in FIGS. 1-8.

FIG. 9 is a flowchart illustrating one embodiment of a method 300 for attaching tissue to a bone using the suture management system illustrated in FIGS. 1-8. In a first step 302, a suture anchor 12 is driven into a bone. The suture anchor 12 may be driven into a bone by, for example, rotating the handle 4 to engage the threads 36 of the suture anchor 12 with the bone. In some embodiments, a pilot hole may be formed in the bone prior to insertion of the suture anchor 12. One or more sutures 14 are coupled to the suture anchor 12. In a second step 304, a force 22 is applied to the proximal sections 20a, 20b of the doors 8a, 8b. The force 22 overcomes the biasing force applied by the springs 30a, 30b and pivots the doors 8a, 8b from a closed position to an open position.

In a third step 306, one or more suture ends 14 are released from a cavity 26 defined by each of the doors 8a, 8b. The suture ends 14 may be coupled to one or more needles 38. In some embodiments, a needle holder is located within the cavity 26 and is configured to maintain the needles 38 in a fixed position. The one or more needles 38 are coupled to one or more suture ends 14a, 14b wrapped around elongate grooves 6a, 6b formed in the handle 4. The suture ends 14a, 14b extend distally along the outer surface of the shaft 10 to the suture anchor 12. After removing the needles 38, in a fourth step 308, the suture ends 14a, 14b are unwound from the elongate grooves 6a, 6b. The handle 4 and the shaft 10 may be discarded after the needles 38 and the suture ends 14a, 14b are removed.

In a fifth step 310, the suture ends 14a, 14b are used to attach one or more tissue sections to a bone. The tissue sections may comprise connective and/or other tissue removed from the bone by an accident, surgery, and/or any other cause. In a sixth step 312, the needles 38 are removed from the suture ends 14a, 14b and the suture 14 is retained in the patient. The suture 14 may comprise a biodegradable suture material.

Figure 10:
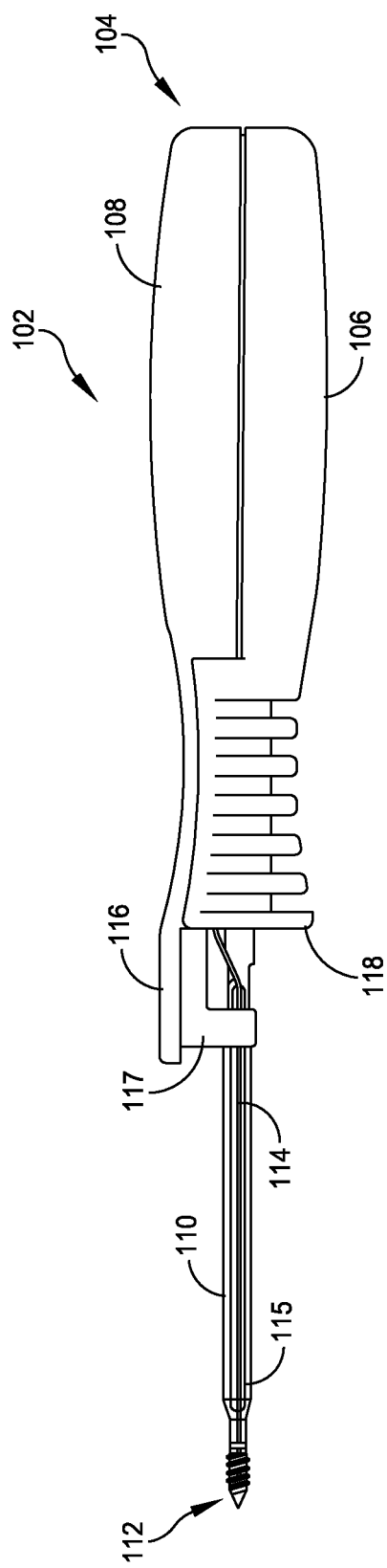
FIG. 10 illustrates one embodiment of a suture management device comprising a first handle portion and a second handle portion.

FIG. 10 illustrates one embodiment of a suture management system 102. The suture management system 102 comprises a handle 104. The handle 104 comprises a first handle portion 106 and a second handle portion 108. The first handle portion 106 is releasably coupled to the second handle portion 108. For example, in some embodiments the first handle portion 106 comprises one or more male mating elements and the second handle portion 108 comprises one or more complimentary female mating elements. A shaft 110 extends from a distal portion of the handle 104. The second handle portion 108 comprises an over-molded extension 116 sized and configured to couple to the shaft 110.

Figure 11:
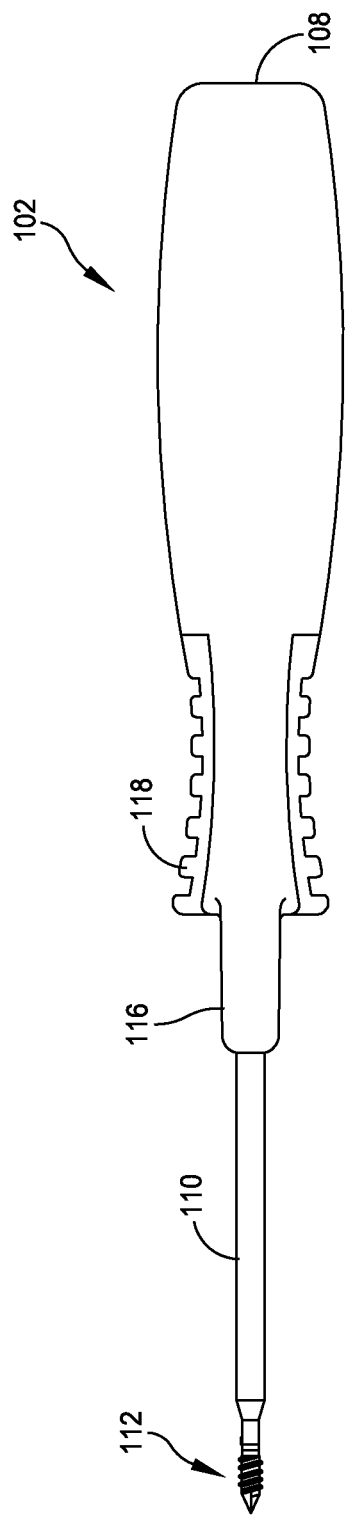
FIG. 11 illustrates a top view of the suture management device of FIG. 10.

In some embodiments, a suture anchor 112 is releasably coupled to the distal end of the shaft 110. One or more sutures 114 extend from the suture anchor 112 proximally along an outer surface of the shaft 110 to the handle 104. In some embodiments, the over-molded extension 116 comprises a clip 117 configured to couple to the shaft 110 and to maintain the sutures 114 against the shaft 110. In some embodiments, the shaft 110 comprises one or more channels 115 sized and configured to receive one or more sutures 114 therein and to allow the suture ends 114a, 114b to sit flush with or below the surface of the shaft 110. The suture ends 114a, 114b extend into the handle 104 and are secured within the handle 104. In some embodiments, one or more handle features 118 are configured to provide a gripping surface to a clinician during implantation of the suture anchor 112. FIG. 11 illustrates a top view of the suture management system 102. As shown in FIG. 11, the over-molded extension 116 extends a predetermined distance onto the shaft 110.

Figure 12:
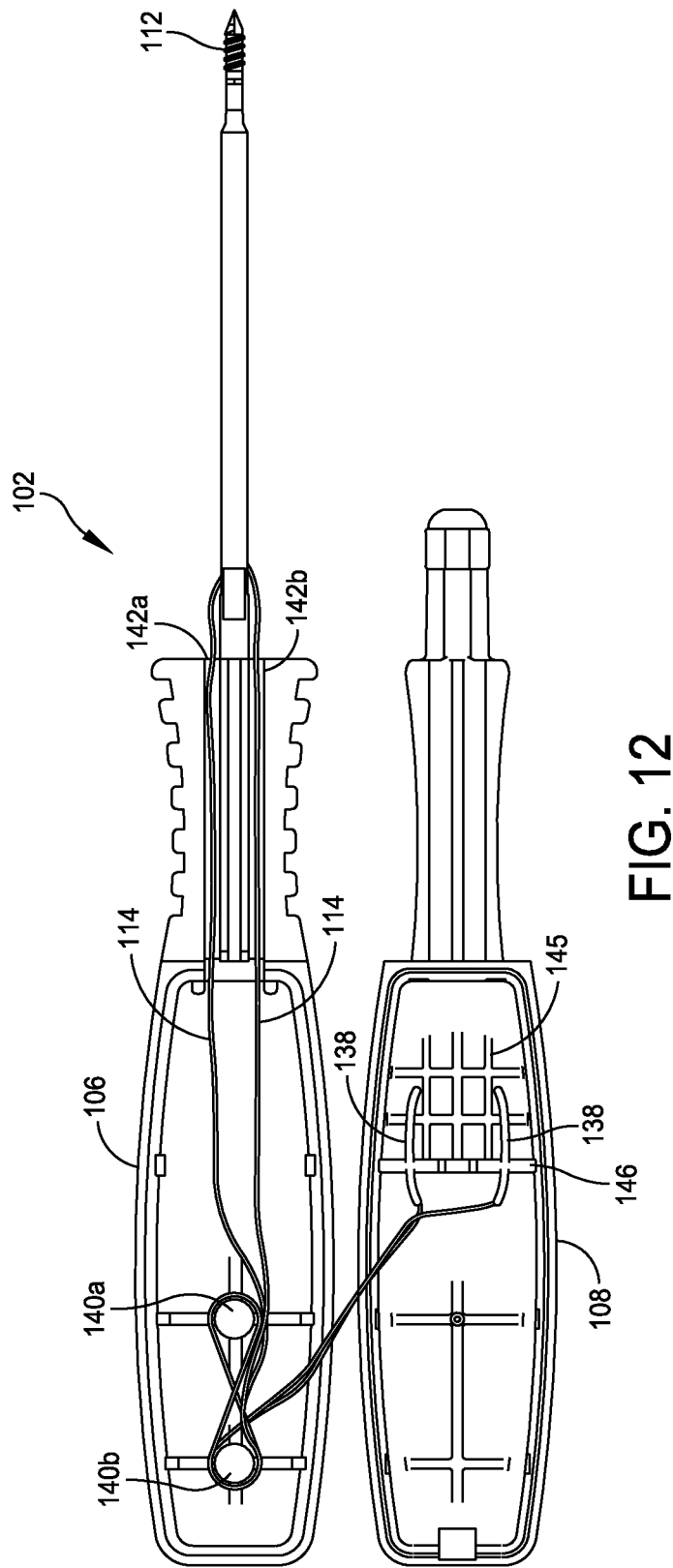
FIG. 12 illustrates one embodiment of the suture management device of FIG. 10 having the first handle portion separated from the second handle portion to deploy a suture having a first end and a second end.

FIG. 12 illustrates one embodiment of the suture management device 102 having the first handle portion 106 separated from the second handle portion 108. The sutures 114a, 114b extend into the handle 104 and wrap around a first post 140a and a second post 140b. The sutures 114a, 114b are wrapped around the posts 140a, 140b to maintain tension on the suture 114 and prevent the suture ends 114a, 114b from tangling. In some embodiments, the posts 140a, 140b comprises a silicone tube (see FIG. 15D) covering the post. The suture ends 114a, 114b are each coupled to a needle 138a, 138b at a proximal end. The needles 138a, 138b are retained within the second handle portion 108. In some embodiments, the needles 138a, 138b may be coupled to a needle holder 146. The needle holder 146 may comprise any suitable needle/suture holder such as, for example, a force-fit suture holder (see FIGS. 27A-27B), a press-fit suture holder (see FIGS. 28A-28B), a magnetic needle holder (see FIGS. 29A-29B), and/or any other suitable suture/needle holder. In some embodiments, the needles 38 may be located within a cavity defined by the second handle portion 108. The posts 140a, 140b and the needle holder 146 maintain the suture ends 114a, 114b in a predetermined arrangement within the handle 104.

When the first handle portion 106 is separated from the second handle portion 108, the suture ends 114a, 114b unravel from the posts 140a, 140b and decouple from the first handle portion 106. Because the suture ends 114a, 114b are wrapped around posts 140a, 140b in a first handle portion 106 and the needles 138 are coupled to a second handle portion 108, the separation of the first handle portion 106 from the second handle portion 108 causes the sutures 114a, 114b to unravel from the posts. The first handle portion 106 and the shaft 110 may be discarded. The needles 138a, 138b are removed from the second handle portion 108 and used to anchor one or more tissue sections to a bone. Once each of the needles 138a, 138b are removed from the second handle portion 108, the second handle portion 108 may be discarded. The first and second handle portions 106, 108 maintain the suture ends 114a, 114b in a predetermined position during deployment of the suture anchor 112 and may be discarded after the suture 114 and the needles 138a, 138b are deployed.

In operation, a clinician implants the suture anchor 112 into a bone using the handle 104 and the shaft 110. The posts 140a, 140b maintain tension on the suture ends 114a, 114b during implantation of the suture anchor 112 and, in conjunction with the clip 117, maintain the suture ends 114a, 114b flush with the shaft 110 during implantation. Once the suture anchor 112 is implanted in the bone, the first handle portion 106 is separated from the second handle portion 108 by, for example, releasing a male mating feature of the first handle portion 106 from a female mating feature of the second handle portion 108. The suture ends 114a, 114b are unwrapped from the posts 140a, 140b by pulling the second handle portion 108 away from the first handle portion 106. The first handle portion 106 and the shaft 110 are discarded. The needles 138a, 138b are removed from the second handle portion 108 and used to attach one or more tissue sections to the bone. After each of the needles 138a, 138b is removed from the second handle portion 108, the second handle portion 108 is discarded.

FIG. 13 illustrates one embodiment of a suture anchor 112. The suture anchor 112 comprises a bone screw having an eyelet 132 (or beam) configured to couple the suture 114 to the suture anchor 112. In some embodiments, the suture 114 comprises a single continuous suture extends through the suture eyelet 132. A first end 114a and a second end 114 extend proximally from the suture anchor 112. The suture anchor 112 further comprises a sharp, distal tip 34 and a plurality of threads 36 to anchor the suture anchor 112 to a bone. In some embodiments, the suture anchor 112 is implanted into a bone by rotating the suture anchor 112 using the handle 104 and the shaft 110. The suture anchor 112 may be detached from the shaft 110 after the suture anchor 112 is implanted into a bone.

FIG. 14 illustrates one embodiment of the suture anchor 112 of FIG. 13 having a suture 114 coupled thereto. The suture 114 is coupled to the suture anchor 112 at a mid-point of the suture 114. A first suture end 114a and a second suture end 114b extend proximally from the suture anchor 112. The first suture end 114a and the second suture end 114b are each coupled to a needle 138 at a proximal end. The suture ends 114a, 114b comprise a sufficient length such that the suture ends 114a, 114b can extend from the suture anchor 112, along the shaft 110, into the handle 104 and about the posts 140a, 140b. In some embodiments, the needles 138 are stored in a needle holder 146 coupled to the second handle portion 108 until the suture ends 114a, 114b are deployed. Although a single suture is illustrated, it will be appreciated that any number of sutures may be coupled to the suture anchor 112.

Figure 15B:
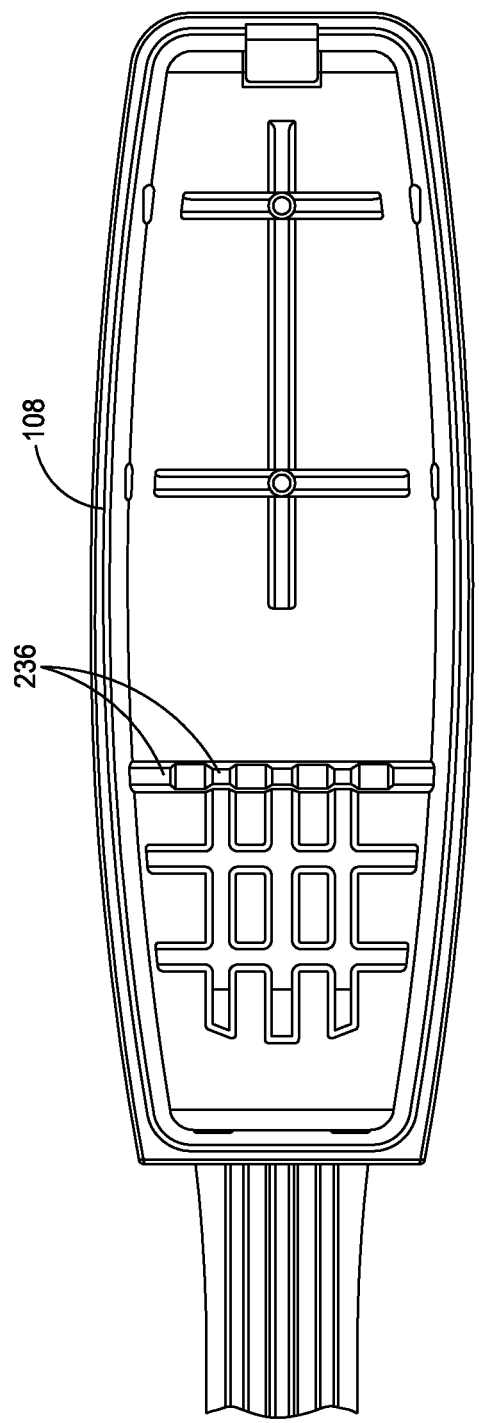
FIGS. 15B-15D illustrate various views of the suture management device of FIG. 15A.
Figure 15C:
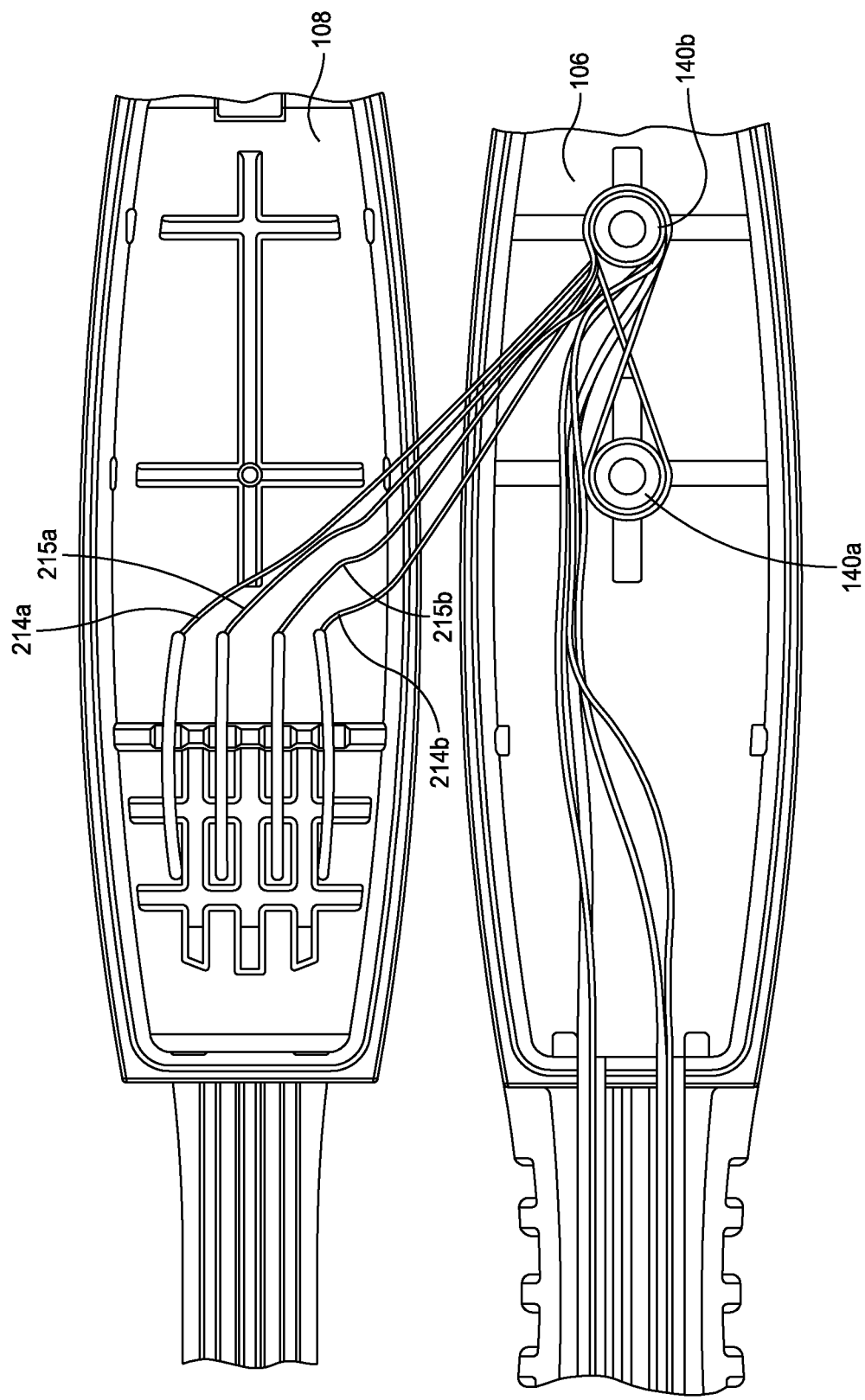
Figure 15D:
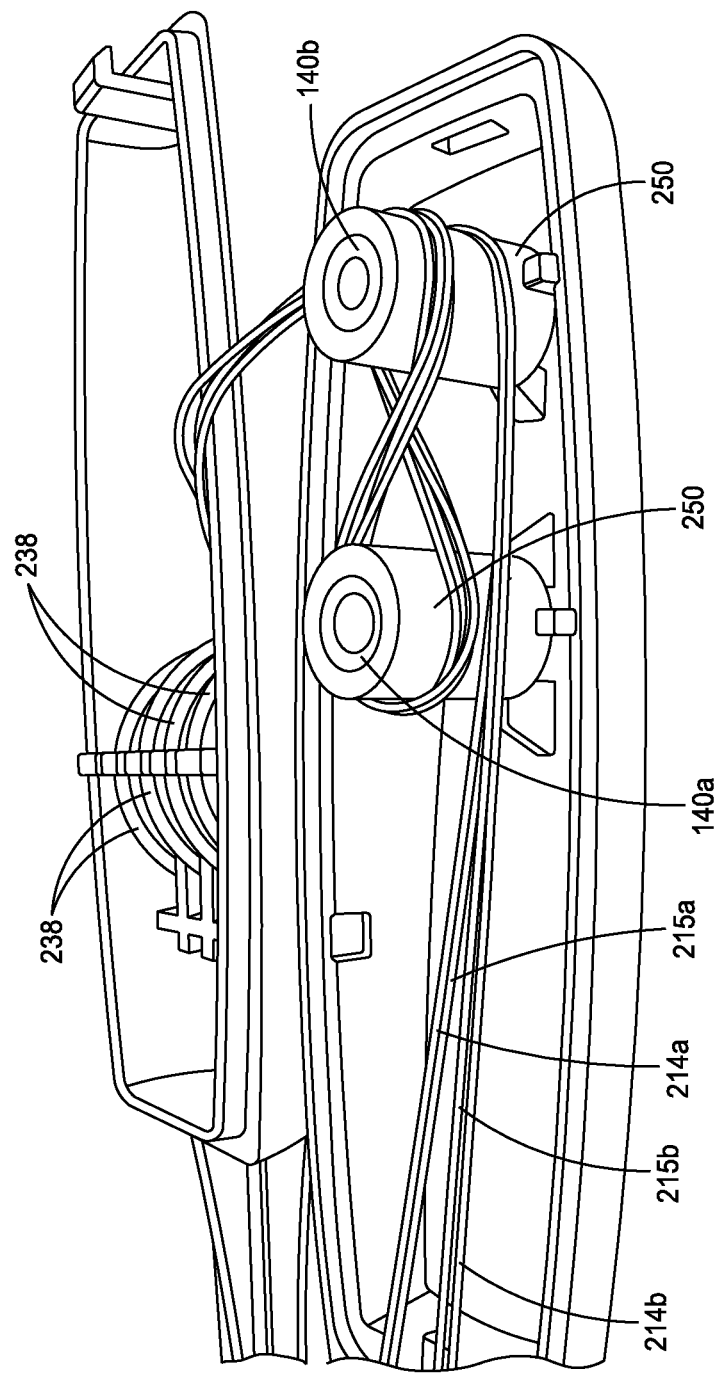

FIGS. 15A-15D illustrate one embodiment of a suture management device 202 comprising a plurality of sutures 214a-214b. The suture management device 202 is similar to the suture management device 102 discussed with respect to FIGS. 9-13 and similar elements are not discussed herein for the purpose of conciseness. In the illustrated embodiment, two sutures 214, 215 extend from the suture anchor 112, along the shaft 110, and into the handle 104. A first end 214a, 215a and a second end 214b, 215b of each of the sutures 214, 215 are wrapped about the posts 140a, 140b. Each of the suture ends 214a-215b comprise a needle 238a-238d coupled to a proximal end. In some embodiments, the needles 238a-238d are coupled to the needle holder 146. When the first handle portion 106 is separated from the second handle portion 108, the plurality of sutures 214, 215 unravel from the posts 140a, 140b. The first handle portion 106 may be discarded. The needles 238a-238d are removed from the second handle portion 108 and the second handle portion 108 may be discarded. FIG. 15D illustrates one embodiment of the suture management device 202 having silicone tubes 250 disposed over the posts 140a, 140b.

FIG. 16 illustrates one embodiment of a suture anchor 212 having a plurality of sutures 214, 215 coupled thereto. Each of the plurality of sutures 214, 215 is coupled to the suture anchor 212. In the illustrated embodiment, each of the sutures 214, 215 are coupled to the suture anchor 212 at a mid-point of the suture 214, 215. The sutures 214, 215 each comprise a first end 214a, 215a and a second end 214b, 215b extending proximally from the suture anchor 212. Each of the proximal end of each of the suture ends 214a-215b are coupled to a needle 238a-238d. The suture anchor 212 may comprise any suitable anchor, such as, for example, a bone screw, a pin, a bone tag, a staple, and/or any other suitable anchor.

Figure 17:
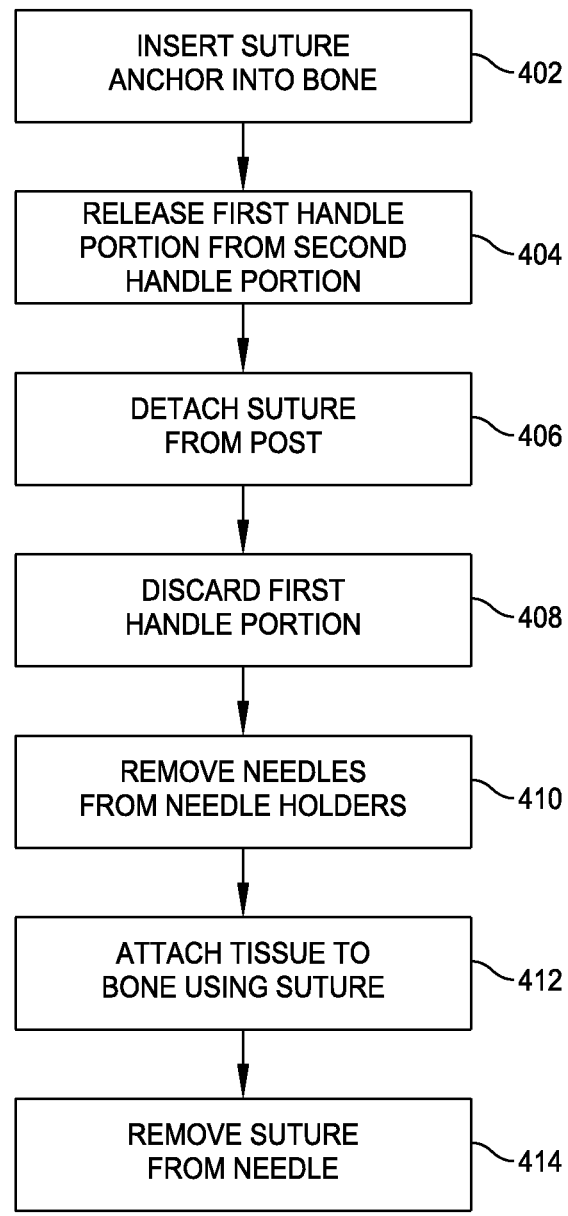
FIG. 17 is a flowchart illustrating one embodiment of a method for attaching tissue to a bone using the embodiments of a suture management device illustrated in FIGS. 10-16.

FIG. 17 is a flowchart illustrating one embodiment of a method 400 for attaching tissue to a bone using the suture management device illustrated in FIGS. 10-16. In a first step 402, a suture anchor 112 is coupled to a bone. The suture anchor 112 may be coupled to a bone using a handle 104 and a shaft 110 of a suture management system 102. The suture anchor 112 may comprise any suitable anchor, such as, for example, a bone screw having a thread 36 that is rotated by the handle 4 and driven into the bone. In some embodiments, a pilot hole is formed in the bone prior to insertion of the suture anchor 112.

In a second step 404, a first handle portion 106 is released from a second handle portion 108. The first and second handle portions 106, 108 are coupled together by, for example, a releasable male mating feature and a female mating feature formed respectively on one of the first or second handle portions 106, 108. The first handle portion 106 and the second handle portion 108 may be disconnected by, for example, forcing the male mating feature and the female mating feature apart. In other embodiments, a release mechanism may release the first and second handle portions 106, 108.

In a third step 406, one or more sutures 114, 214, 215 unravel from a first post 140a and a second post 140b formed on the inner surface of the first handle portion 106. The suture ends 114a, 114b extend distally from the posts 140a, 140b along the shaft 110 to the suture anchor 112. The suture ends 114a, 114b further extend proximally to a plurality of needles 138a, 138b coupled to the second handle portion 108. In some embodiments, the suture ends 114a, 114b unravel from the posts 140a, 140b when the first handle portion 106 and the second handle portion 108 are separated as the needles 138a, 138b are coupled to the second handle portion 108 and exert a force on the suture ends 114a, 114b, causing the suture 114 to unravel from the posts 140a, 140b. In a fourth step 408, the first handle portion 106 and the shaft 110 may be discarded after the sutures 114a, 114b are disconnected from the posts 140a, 140b.

In a fifth step 410, the needles 138a, 138b are removed from the second handle portion 108. In some embodiments, the needles 138a, 138b are removed from a needle holder 146 configured to maintain the needles 138a, 138b in a fixed position. In other embodiments, the needles 138a, 138b are loosely stored within the second handle portion 108. The second handle portion 108 may be discarded after the needles 138a, 138b are decoupled from the second handle portion 108. In a sixth step 412, tissue, such as, for example, connective tissue, may be coupled to the bone using the suture ends 114a, 114b and the needles 138a, 138b. After the tissue is coupled to the bone, the needles 138a, 138b may be removed from the suture ends 114a, 114b in a seventh step 414. The suture 114 may comprise biodegradable sutures configured to be retained within a patient.

Figure 18:
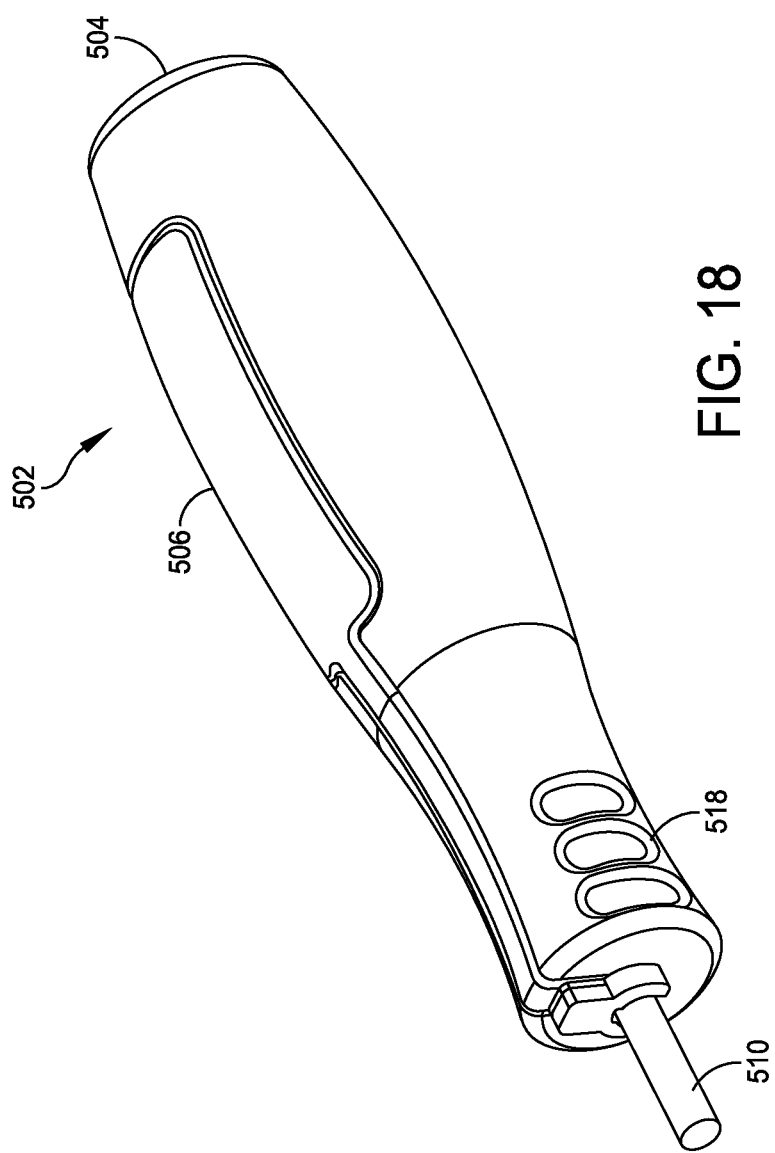
FIG. 18 illustrates one embodiment of a suture management device comprising a releasable cartridge.
Figure 19:
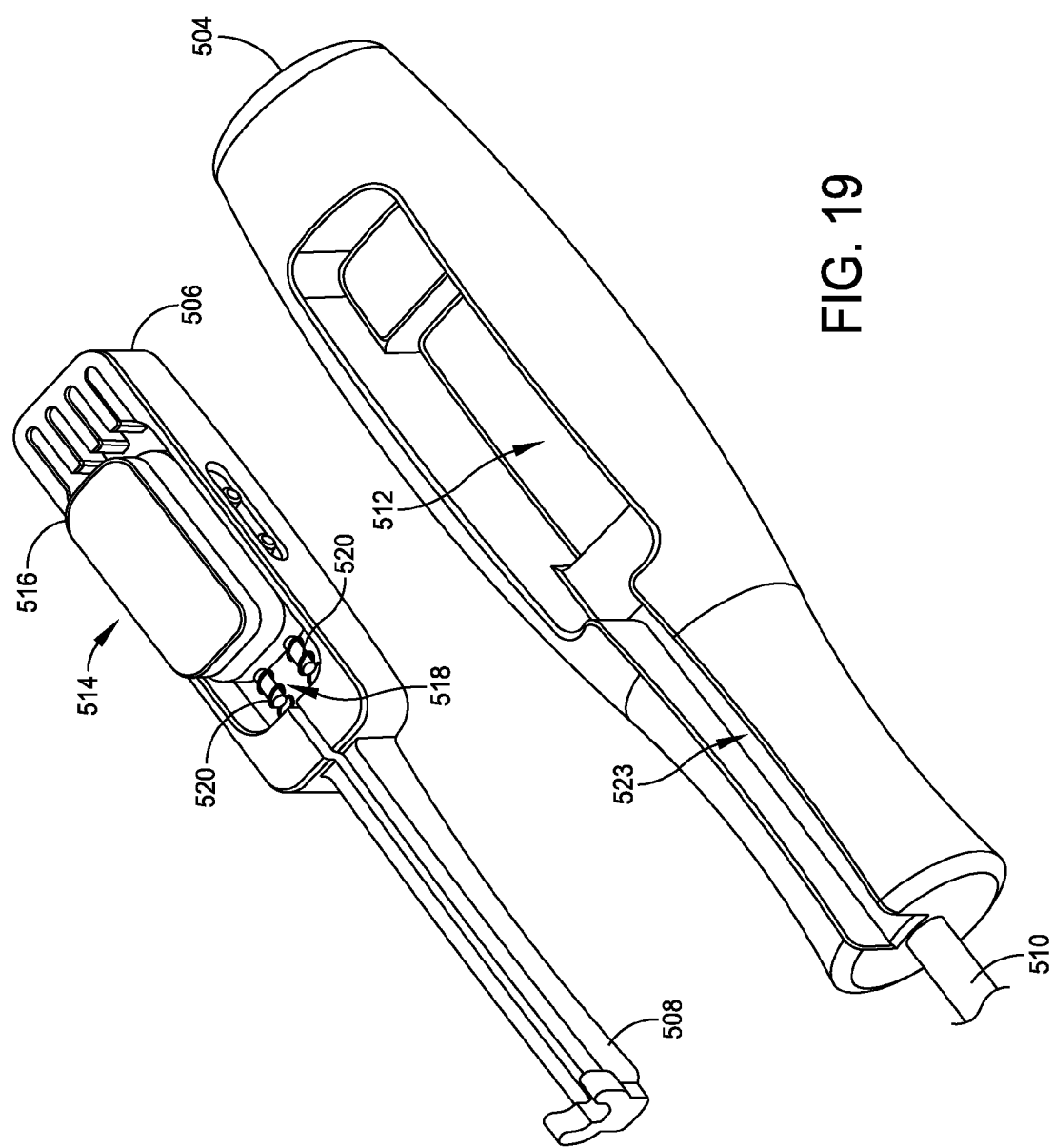
FIG. 19 illustrates the suture management device of FIG. 18 having the releasable cartridge separated from a handle.

FIG. 18 illustrates one embodiment of a suture management system 502. The suture management system 502 comprises a handle 504. A shaft 510 extends distally from the handle 504. The shaft 510 may be coupled to a suture anchor, such as, for example, the suture anchor 12 illustrated in FIGS. 7 and 8, at a distal end. The handle 504 comprises a releasable cartridge 506 couple thereto. A suture, such as, for example, the suture 14, extends from the distal end of the shaft 510 (for example, from a suture anchor) along the outer surface of the shaft 510 and into an area defined between the releasable cartridge 506 and the handle 504. FIG. 19 illustrates the suture management system 502 having the releasable cartridge 506 disengaged from the handle 504. As shown in FIG. 19, the releasable cartridge 506 comprises a suture tensioning assembly 514 configured to receive one or more sutures and maintain tension on the sutures. The handle 504 defines a cavity 512 sized and configured to receive the suture tensioning assembly 514 and the releasable cartridge 506 therein.

Figure 20:
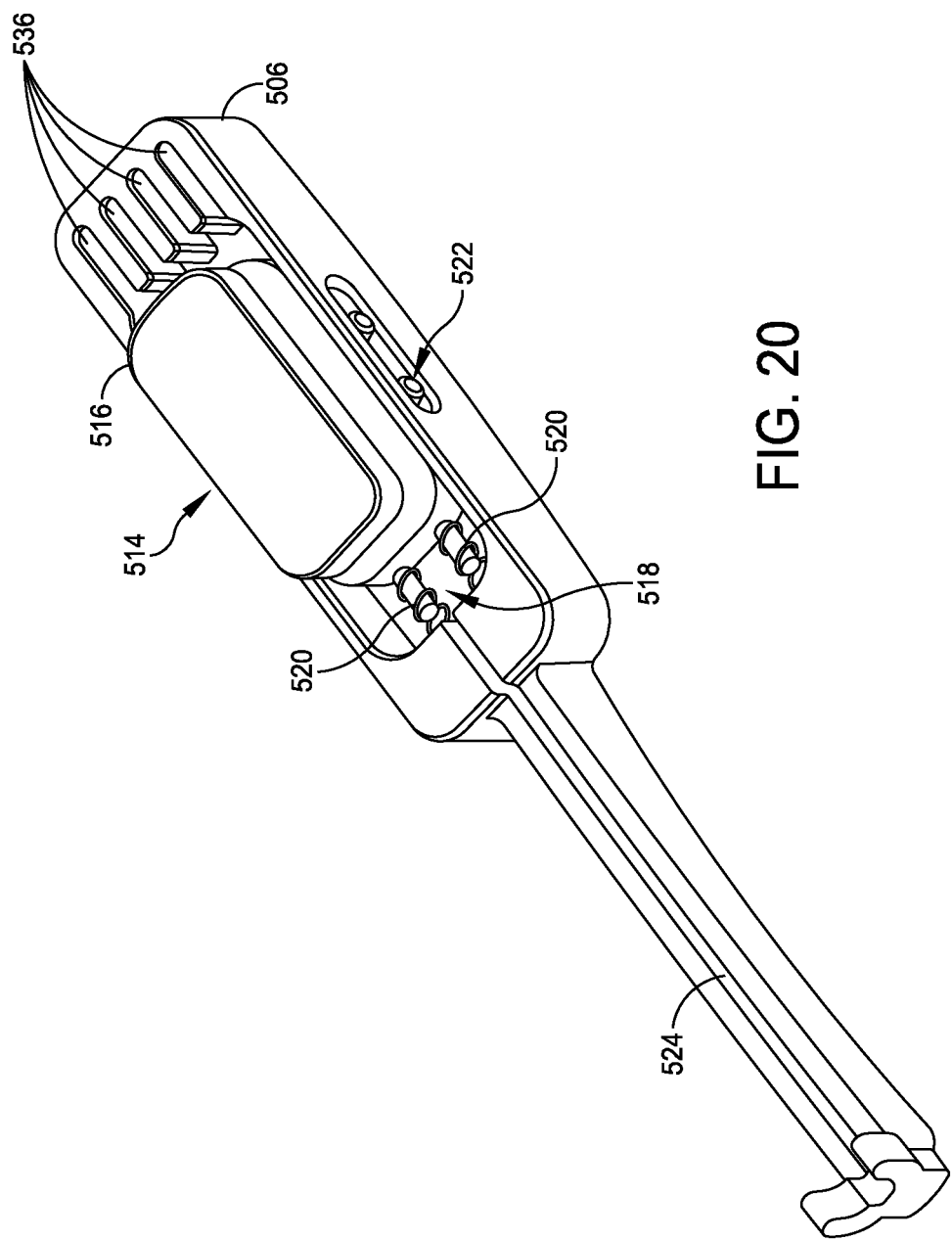
FIG. 20 illustrates one embodiment of a tensioning device of the suture management system of FIG. 18.
Figure 21:
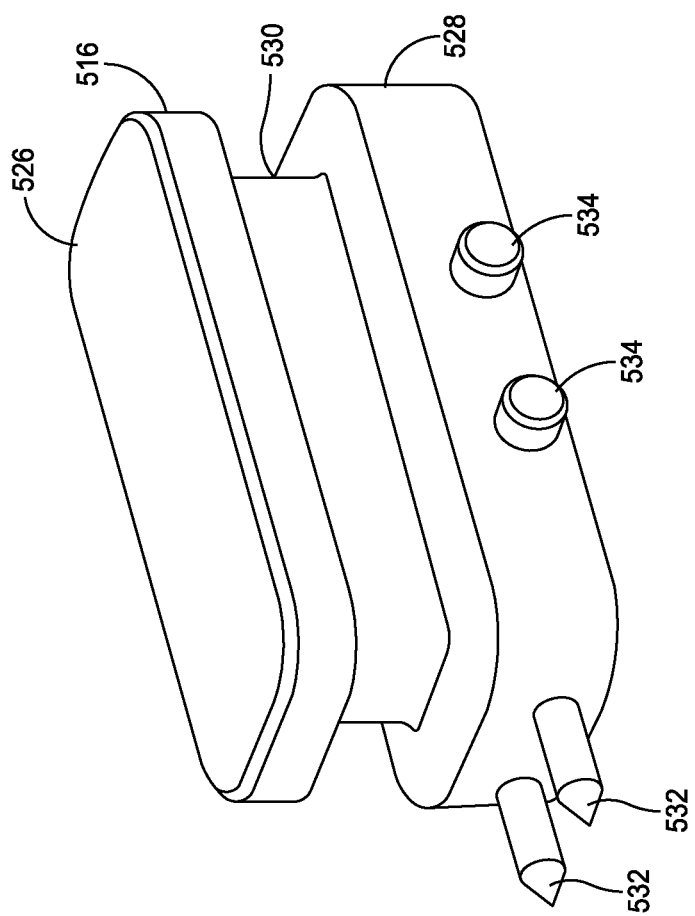
FIG. 21 illustrates one embodiment of a spring tension slider of the suture management system of FIG. 18.

FIG. 20 illustrates one embodiment of the releasable cartridge 506 having a suture tensioning assembly 514 coupled thereto. The suture tensioning assembly 514 is configured to receive one or more sutures and maintain tension on the sutures. The suture tensioning assembly 514 comprises a tensioning block 516. FIG. 21 illustrates one embodiment of the tensioning block 516. With reference to FIGS. 19-21, the suture tensioning assembly 514 is described. The releasable cartridge 506 comprises a suture block cavity 518 sized and configured to slideably receive the tensioning block 516 therein. A plurality of springs 520 are configured to apply a proximal force to the tensioning block 516. In some embodiments, the tensioning block 516 comprises spring location bosses (or protrusions) 532 configured to interface with and maintain the plurality of springs 520 when the tensioning block 516 is inserted into the block cavity 518. The tensioning block 516 may comprise one or more side protrusions 534 sized and configured to be received within a slot 522 formed in a side of the releasable handle 506. The side protrusions 534 and the slot 522 limit the tensioning block 516 to linear movement in a proximal/distal direction.

In operation, the tensioning block 516 is configured to receive one or more sutures and to maintain the position of the sutures prior to the releasable cartridge 506 being separated from the handle 504. The tensioning block 516 comprises a top portion 526 and a bottom portion 528. A suture receiving portion 530 is located between the top portion 526 and the bottom portion 528. The suture receiving portion 530 comprises a diameter less than the top portion 526 and the bottom portion 528. One or more sutures extend along an outer surface of a shaft 510 and into the suture cavity 524 formed in an longitudinal portion 508 of the releasable cartridge 506. The one or more sutures are wrapped around the tensioning block 516 to maintain tension on the sutures. In some embodiments, the tensioning block 516 is compressed distally when the sutures are wrapped around the tensioning block 516 and released, causing the springs 520 to apply a proximal force to the tensioning block 516 and maintaining tension on the sutures.

In some embodiments, the proximal end of each of the sutures is coupled to a needle (not shown). In some embodiments, the releasable cartridge 506 comprises a needle holder 536. The needle holder 536 may comprise, for example, a force-fit suture holder (see FIGS. 27A-27B), a press-fit suture holder (see FIGS. 28A-28B), a magnetic needle holder (see FIGS. 29A-29B) and/or any other suitable suture/needle holder. The needles may be coupled to the needle holder 536. The needle holder 536 maintains the needles in a fixed position until the sutures have been released from the tensioning block 516. In some embodiments, the needle holder 536 is omitted and the needles are loosely stored within a cavity defined by the handle 504 and/or the releasable cartridge 506.

Figure 22:
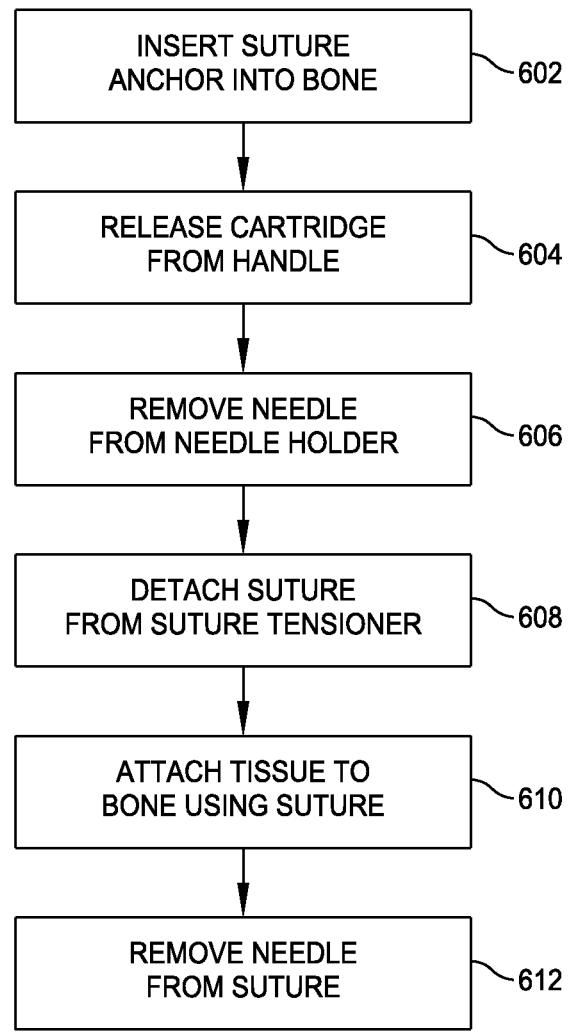
FIG. 22 is a flowchart illustrating one embodiment of a method for attaching tissue to a bone using the embodiments of a suture management device illustrated in FIGS. 18-21.

In operation, the tensioning block 516 and the releasable cartridge 506 maintain one or more sutures during implantation of a suture anchor (such as, for example, the suture anchor 12 illustrated in FIGS. 7-8). FIG. 22 is a flowchart illustrating one embodiment of a method 600 for attaching tissue to a bone using the suture management device illustrated in FIGS. 18-21. In a first step 602, a suture anchor is driven into a bone. For example, a suture anchor may be coupled to the distal end of the shaft 510 of the suture management system 502. The handle 504 is rotated to drive the suture anchor into the bone. The suture anchor is released from the shaft 510 after implantation of the anchor in the bone. In a second step 604, the releasable cartridge 506 is released from the handle 504. The releasable cartridge 506 may be removed from the handle 504 by, for example, gripping the extension 508 and pulling the releasable cartridge 506 to separate the releasable cartridge 506 from the handle 504. The handle 504 may be discarded after the releasable cartridge 506 is separated therefrom.

In an optional third step 606, one or more needles are separated from a needle holder 536 formed in the releasable handle 506. The needles are coupled to sutures and are maintained in a fixed position by the needle holder 536. After the needles are removed from the needle holder 536, in a fourth step 608, the sutures are unwrapped from a suture tensioning block 516. The releasable cartridge 506 may be discarded after unwrapping the sutures.

Figure 23:
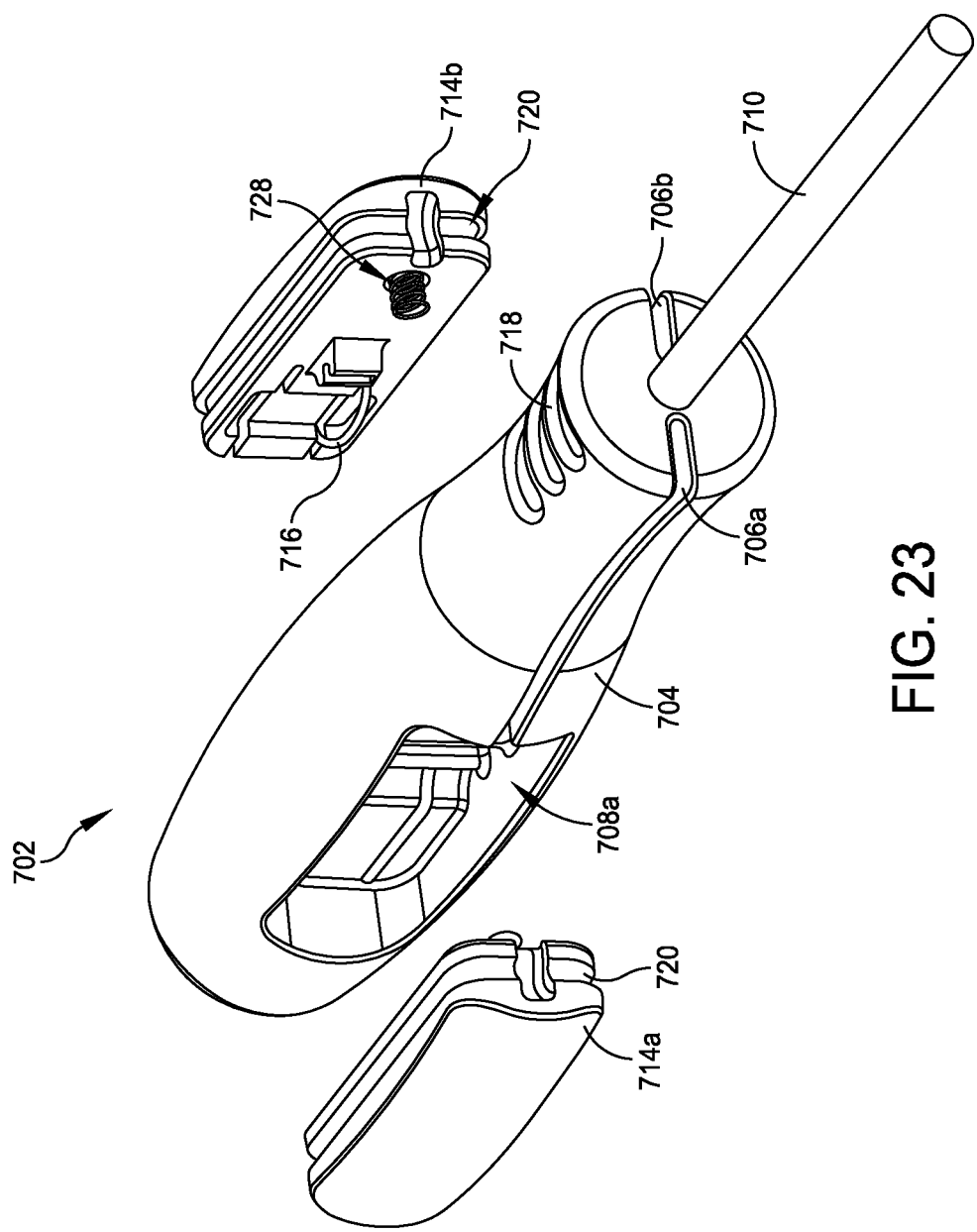
FIG. 23 illustrates one embodiment of a suture management device comprising a first releasable cartridge and a second releasable cartridge.

In a fifth step 610, tissue, such as, for example, connective tissue, may be coupled to the bone using the sutures and the needles. After the tissue is coupled to the bone, the needles may be removed from the sutures in a sixth step 612. The sutures may comprise biodegradable sutures configured to be retained within the patient FIG. 23 illustrates one embodiment of a suture management system 702. The suture management system 702 comprises a handle 704. A shaft 710 extends distally from the handle 704. A suture anchor, such as, for example, the suture anchor 12 illustrated in FIGS. 7-8, may be coupled to the distal end of the shaft 710. A plurality of sutures, such as, for example, the sutures 14a, 14b, extend from the distal end of the shaft 710, for example from the suture anchor, to the handle 704. The handle 704 comprises a first suture channel 706a and a second suture channel 706b configured to receive one or more suture ends therein.

The handle 704 comprises a first releasable cartridge 714a and a second releasable cartridge 714b. The first and second releasable cartridges 714a, 714b are sized and configured to be received within cartridge cavities 708a, 708b formed in the handle. The releasable cartridges 714a, 714b each comprise a suture channel 720. The ends of the suture are configured to extend through one of the first or second suture channels 706a, 706b and are wrapped around one of the releasable cartridges 714a, 714b within the suture channel 720. The releasable cartridges 714a, 714b are coupled to the handle 704 and maintain tension on the suture ends. When the releasable cartridges 714a, 714b are decoupled from the handle 704, the sutures can be unwound from the releasable cartridges 714a, 714b and used to attached one or more tissue sections to a bone. Each of the suture ends is coupled to a needle at a proximal end.

In some embodiments, the releasable cartridges 714a, 714b comprise a needle holder 716 configured to receive one or more needles therein. The needle holders 716 maintain the needles in a fixed position until the releasable cartridges 714a, 714b are decoupled from the handle 704 and the suture ends unwound from the suture channels 720. In some embodiments, the needle holders 716 comprise a force fit needle holder. In other embodiments, the needle holders 716 comprise a material configured to receive a sharp end of a needle therein, such as, for example, a silicone material. In some embodiments, the needles are loosely stored within one or more cavities defined by the releasable cartridges 714a, 714b and/or the handle 704.

Figure 24:
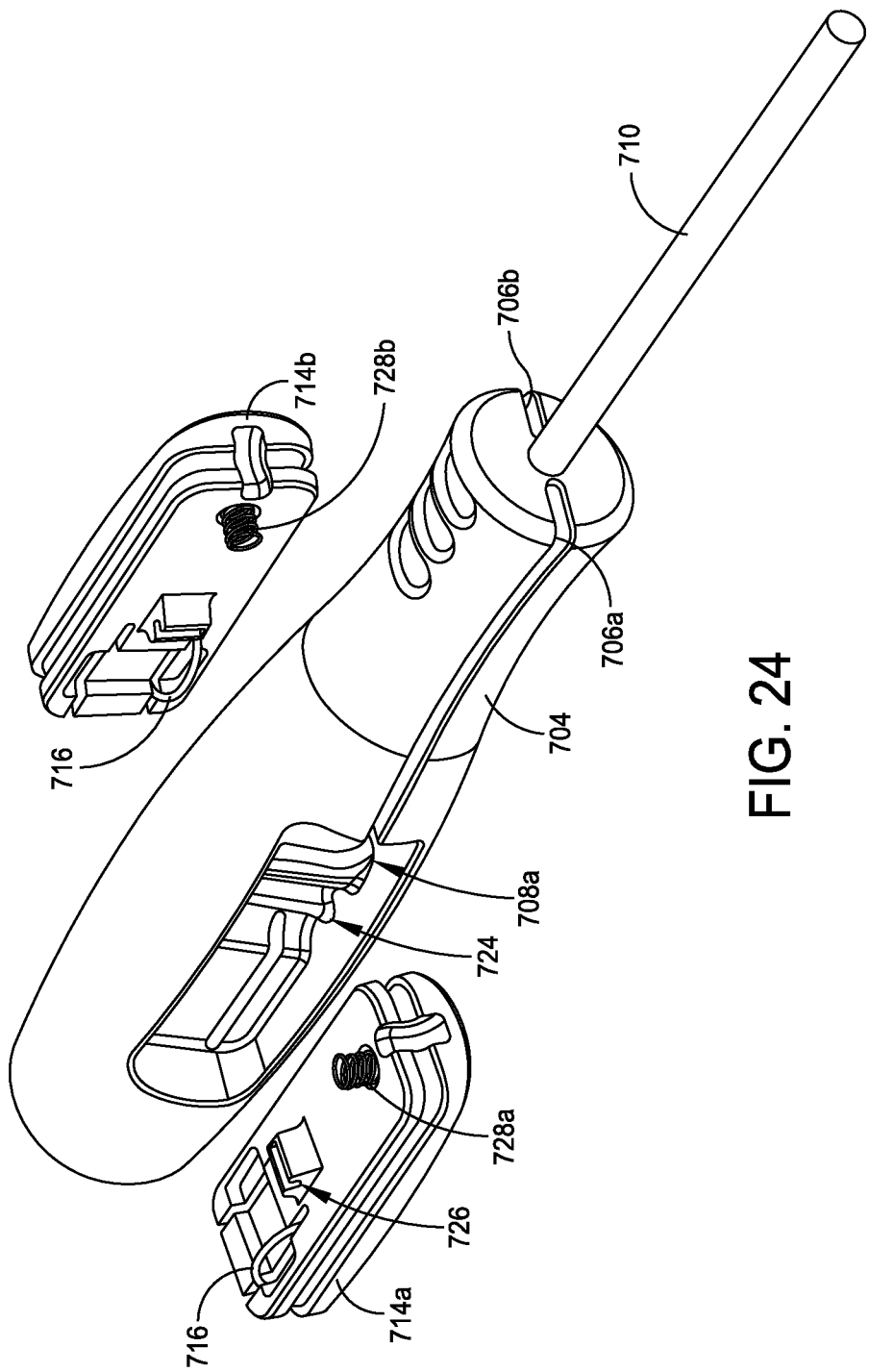
FIG. 24 illustrates the suture management device of FIG. 23 having a first mating feature and a second mating feature for coupling the first and second releasable cartridges to the handle.

FIG. 24 illustrates one embodiment of the suture management system 702 illustrating a side-view of one of the releasable cartridges 714a. Each of the releasable cartridges 714a, 714b comprises a mating feature 726 configured to couple to a mating feature 724 formed in one of the cartridge cavities 708a, 708b of the handle 704. In some embodiments, the mating feature 726 formed on the releasable cartridge 714a comprises a female mating feature and the feature 724 formed in the cartridge cavity 708a comprises a male mating feature. In some embodiments, the mating feature 726 comprises a male mating feature and the mating feature 724 comprises a female mating feature.

Figure 25:
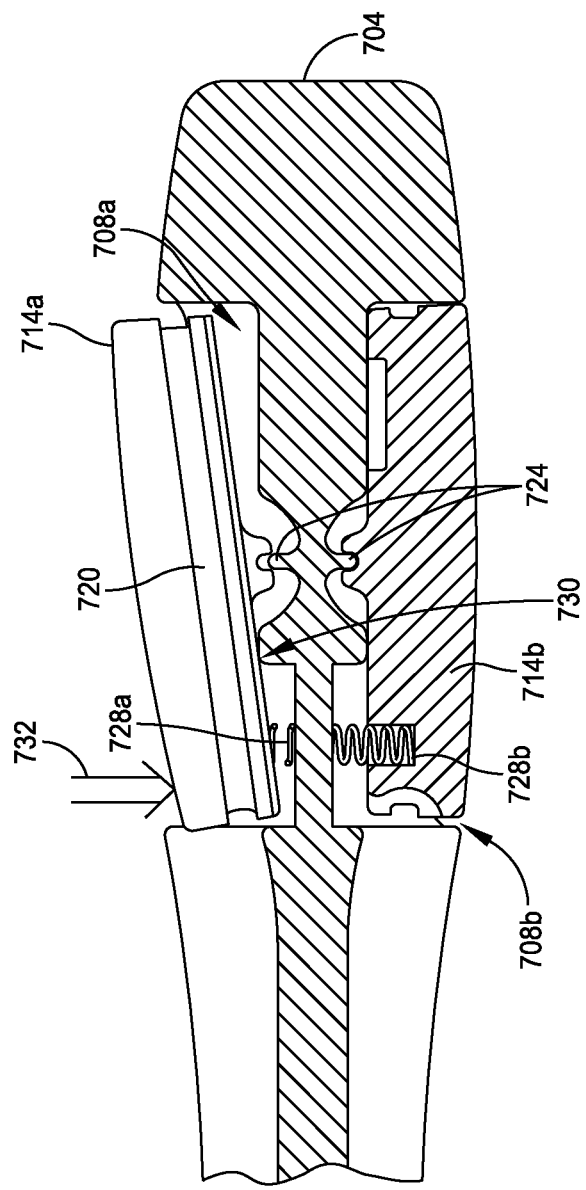
FIG. 25 illustrates a cross-sectional view of the suture management device of FIG. 23 having a plurality of springs configured to maintain the releasable cartridges until a predetermined force is applied.

In operation, one or more sutures are wrapped around one of the releasable cartridges 714a, 714b, which are then coupled to the handle 704. The mating feature 724 in the cartridge cavity 708 couples to the mating feature 726 formed on the releasable cartridges 714a, 714b and maintains the releasable cartridges 714a, 714b in contact with the handle 704. As shown in FIG. 25, a user may apply a force 732 to a distal portion of the releasable cartridges 714a, 714b. The force 732 causes the releasable cartridge 714a to pivot about a pivot point 730. The mating feature 726 is rotated out of contact with the mating feature 724, and the releasable cartridge 714a is released from the handle 704. After the releasable cartridge 714a has been decoupled from the handle 704, the one or more sutures may be unwrapped from the releasable cartridge 714.

In some embodiments, a spring 728a, 728b is coupled to the releasable cartridge 714a, 714b. The springs 728a, 728b are configured to prevent the releasable cartridges 714a, 714b from pivoting about the pivot point 720 until a minimum force 732 is applied to the distal end of the releasable cartridges 714a, 714b. In some embodiments, the releasable cartridges 714a, 714b each comprise a spring pocket 734 sized and configured to receive a spring 728a, 728b therein. The springs 728a, 728b may be press fit into the spring pockets and/or maintained in the spring pockets 734 by any suitable means.

Figure 26:
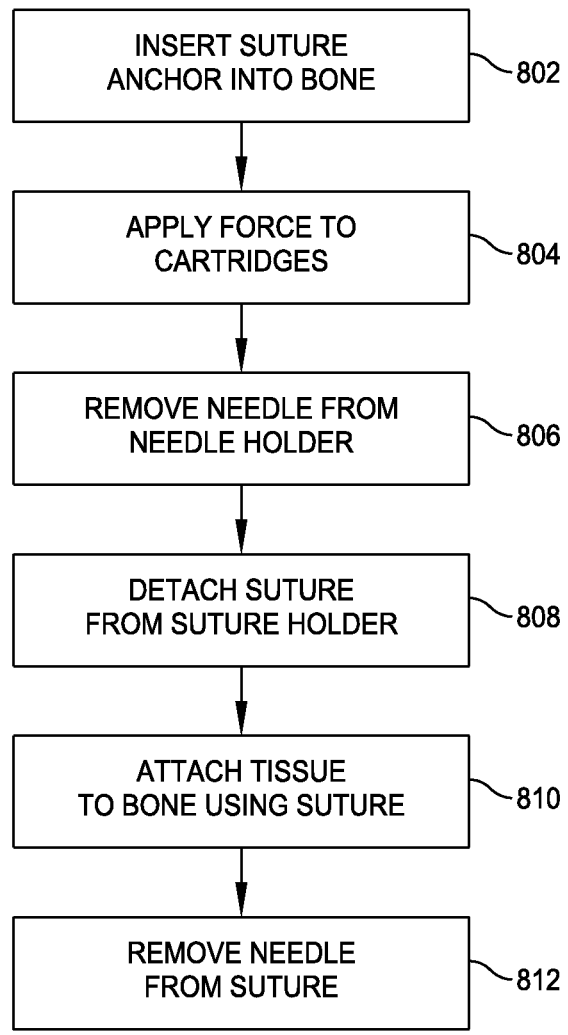
FIG. 26 is a flowchart illustrating one embodiment of a method for attaching tissue to a bone using the suture management device illustrated in FIGS. 23-25.

FIG. 26 is a flowchart illustrating one embodiment of a method 800 for deploying one or more sutures using the suture management system 702 illustrated in FIGS. 23-25. In a first step 802, a suture anchor is driven into a bone. For example, a suture anchor may be coupled to the shaft 710 of the suture management system 702. The handle 704 is rotated to drive the suture anchor into the bone. The suture anchor is decoupled from the shaft 710 after implantation into the bone. In a second step 804, a force 732 is applied to a distal portion of a releasable cartridge 714a, 714b coupled to the handle 704. The force 732 causes the releasable cartridge 714a, 714b to rotate and release from the handle 704. The handle 704 may be discarded after the releasable cartridges 714a, 714b are separated therefrom.

In a third step 806, one or more needles are removed from a needle holder 716 coupled to the releasable cartridges 714a, 714b. The needles are coupled to sutures and are maintained in a fixed position by the needle holders 716. After removing the needles from the needle holders 716, in a fourth step 808, the sutures are unwound from the suture channels 720 formed in the releasable cartridges 714a, 714b. The releasable cartridges 714a, 714b may be discarded after the sutures and the needles have been removed therefrom.

In a fifth step 810, one or more tissue sections are attached to the bone using the needles and sutures. The sutures are anchored to the bone by the suture anchor. After the needle has been passed through the one or more tissue sections a sufficient number of times to couple the tissue to the bone, the needle may be removed from the suture in a sixth step 812.

Figure 27A:
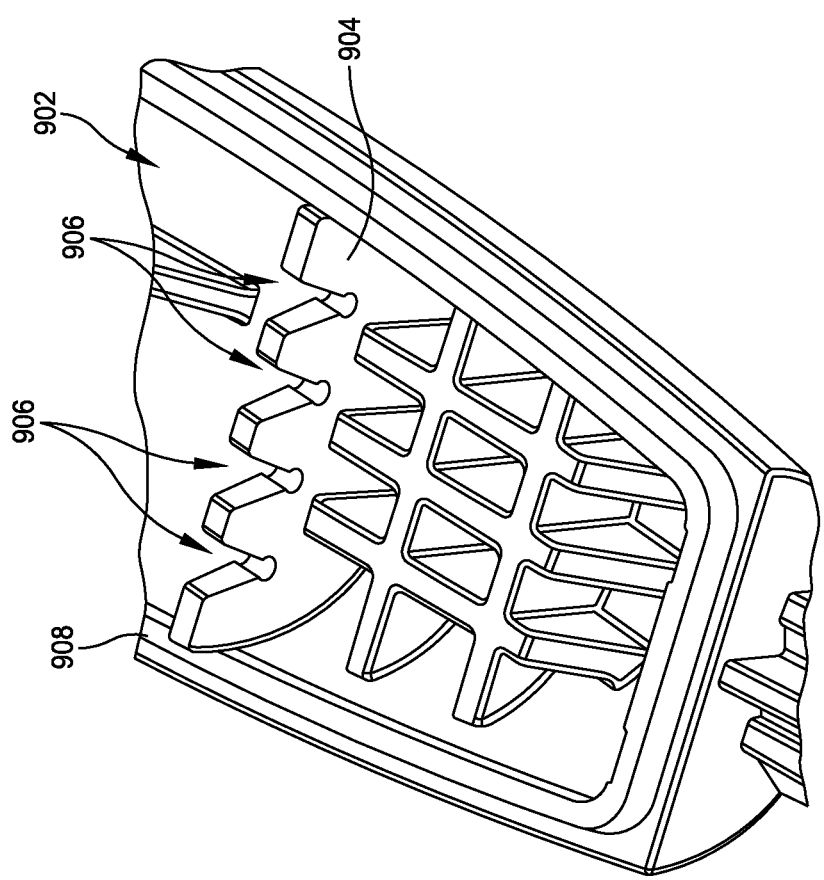
FIG. 27A illustrates one embodiment of a force fit suture holder.
Figure 27B:
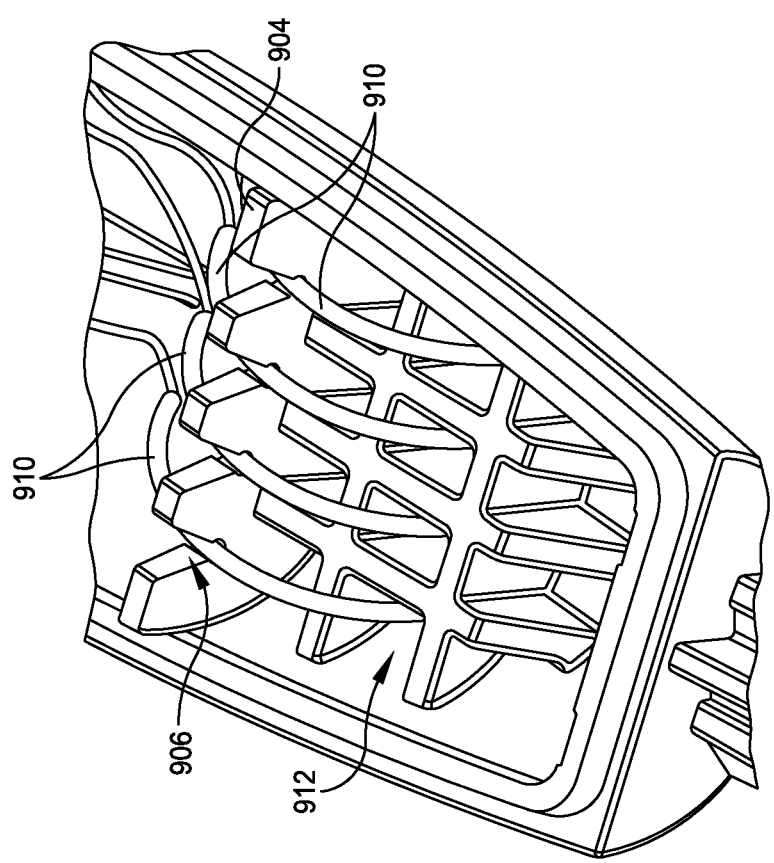
FIG. 27B illustrates the force fit suture holder of FIG. 27A having a plurality of needles coupled thereto.

FIGS. 27A-29B illustrate various embodiments of suture holders that may be used in conjunction with the suture management systems illustrated in FIGS. 1-26. FIG. 27A illustrates one embodiment of a press-fit suture holder 902. The press-fit suture holder 902 comprises a base 904 having a plurality of needle slots 906 formed therein. Each of the plurality of needle slots 906 are sized and configured to receive a needle 910 (see FIG. 27B) therein and to maintain the needle 910 in a fixed position. The press-fit suture holder 902 is illustrated mounted in a handle body 908, although it will be appreciated that the press-fit suture holder 902 may be mounted on any suitable portion of a suture management system, such as, for example, a pivoting door 8a, 8b, a detachable handle body 108, and/or a releasable cartridge 506, 714a, 714b. As shown in FIG. 27B, the press-fit suture holder 902 maintains a plurality of needles 910 in a fixed position. A user may remove the needles 910 from the needle slots 906 and discard the handle body 908.

FIGS. 28A and 28B illustrate one embodiment of a force-fit suture holder 1002. The force-fit suture holder 1002 comprises a material pad 1004 configured to receive a plurality of needles 1010 therein. The needles 1010 comprise a sharp end that is forced into the material pad 1004 and maintained in a fixed position. The material pad 1004 may comprise any suitable material, such as, for example, silicone. The material pad 1004 may be mounted in any suitable portion of a suture management system, such as, for example, a pivoting door 8a, 8b, a detachable handle body 108, and/or a releasable cartridge 506, 714a, 714b.

Figure 29B:
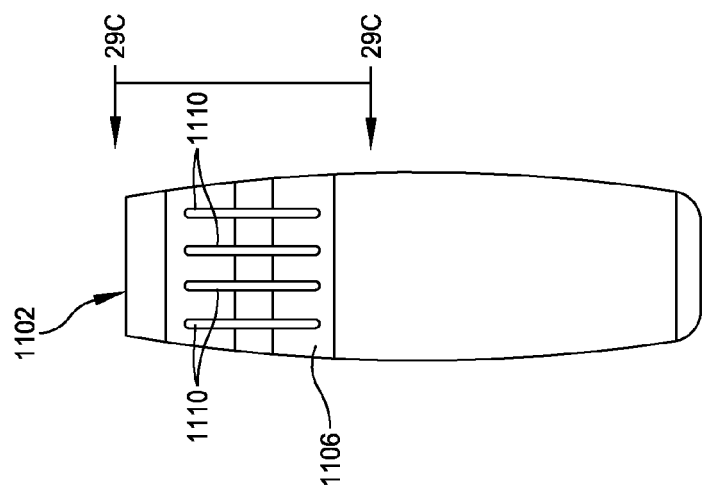
FIG. 29B illustrates the magnetic suture holder of FIG. 29A having an over-molded plastic cover.
Figure 29A:
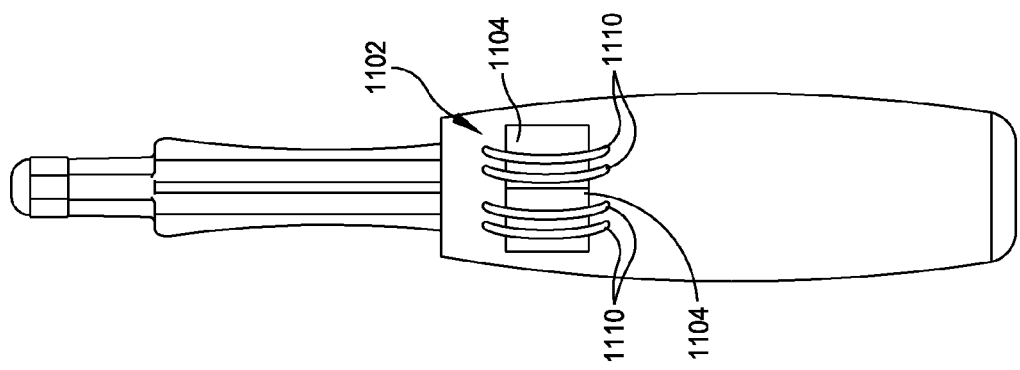
FIG. 29A illustrates one embodiment of a magnetic suture holder.

FIGS. 29A-29C illustrate one embodiment of a magnetic suture holder 1102. The magnetic suture holder 1102 comprises one or more magnets 1104. The magnets 1104 are configured to maintain a plurality of needles 1110 in a fixed position. The magnets 1104 may comprise an over molded plastic cover 1106 (see FIG. 29B). The over molded plastic cover 1106 is configured to match an arc geometry of the needles 1110. The arc geometry of the molded plastic 1106 may be identical to the arc geometry of the needles 1110 to allow for each needle 1110 to sit flush in the handle. A magnetic force generated by the magnets 1104 maintains the needles 1110 in a fixed position. The magnetic suture holder 1102 may be mounted in any suitable portion of a suture management system, such as, for example, a pivoting door 8a, 8b, a detachable handle body 108, and/or a releasable cartridge 506, 714a, 714b.

Although the subject matter has been described in terms of exemplary embodiments, it is not limited thereto. Rather, the appended claims should be construed broadly, to include other variants and embodiments, which may be made by those skilled in the art.

What is claimed is:

1. A suture management device, comprising:
   a handle defining at least a first door cavity;
   a shaft extending distally from the handle;
   a suture anchor coupled to a distal end of the shaft, wherein the suture anchor is configured to couple one or more sutures to a bone; and
   a first releasable door sized and configured to fit within the first door cavity, the first releasable door being releasably coupled to the handle, the first releasable door defining a suture channel, wherein the suture channel extends longitudinally about the circumference of the releasable door, wherein the suture channel is configured to receive the one or more sutures therein.

2. The suture management device of claim 1, further comprising:
   a first mating feature coupled to the handle within the first door cavity; and
   a second mating feature coupled to the first releasable door, wherein the first and second mating features are configured to releasably couple the first releasable door to the handle.

3. The suture management device of claim 2, wherein the first and second mating feature are released by applying a force to a proximal portion of the first releasable door to rotatably decouple the first and second mating features.

4. The suture management device of claim 2, further comprising a spring coupled to the first releasable door, wherein the spring is configured to apply a biasing force to the first releasable door.

5. The suture management device of claim 2, comprising a needle holder coupled to the first releasable door.

6. The suture management device of claim 1, wherein the handle defines a second door cavity, the suture management device further comprising a second releasable door sized and configured to fit within the second door cavity, the second releasable door being releasably coupled to the handle, the second releasable door defining a suture channel, wherein the suture channel extends longitudinally about the circumference of the second releasable door.

7. The suture management device of claim 1, comprising a suture tensioner coupled to the first releasable door, wherein the suture tensioner is sized and configured to be received within the first door cavity, and wherein the suture tensioner defines the suture channel and is configured to maintain tension on the one or more sutures.

8. The suture management device of claim 7, wherein the suture tensioner comprises:

a tensioning block slideably coupled to the second releasable door; and
   at least one spring configured to apply a proximal force to the tensioning block.

9. The suture management device of claim 8, wherein the tensioning block comprises at least one side protrusion sized and configured to interface with a slot formed in the second releasable door, wherein the side protrusion is configured to limit the tensioning block to proximal-distal linear movement.

10. The suture management device of claim 8, wherein the tensioning block comprises a top section, a bottom section, and a middle section, wherein the middle section comprises a diameter less than the top section and the bottom section, and wherein the middle section defines the suture channel.

11. The suture management device of claim 7, comprising a needle holder coupled to the first releasable door, wherein the needle holder is configured to maintain one or more needles coupled to the one or more sutures in a fixed position.

12. The suture management device of claim 7, wherein the first releasable door comprises a distal extension coupled to the shaft.

13. A system comprising:
    a suture management device, comprising
       a handle defining at least a first door cavity;
       a shaft extending distally from the handle;
       a suture anchor coupled to a distal end of the shaft; and
       a first releasable door sized and configured to fit within the first door cavity, the first releasable door being releasably coupled to the handle, the first releasable door defining a suture channel, wherein the suture channel extends longitudinally about the circumference of the first releasable door;
    one or more sutures coupled to the suture anchor, the one or more sutures extending proximally from the suture anchor, and wherein at least a first end of each of the one or more sutures is coupled to the suture channel; and
    one or more needles, wherein each of the one or more needles is coupled to a proximal end of the one or more sutures.

14. The system of claim 13, wherein the suture management system comprises:
    a first mating feature coupled to the handle within the first door cavity; and
    a second mating feature coupled to the first releasable door, wherein the first and second mating features are configured to releasably couple the first releasable door to the handle.

15. The system of claim 13, wherein the suture management system comprises a suture tensioner coupled to the first releasable door, wherein the suture tensioner is sized and configured to be received within the first door cavity, and wherein the suture tensioner defines the suture channel and is configured to maintain tension on the one or more sutures.

* * * * *